(12) United States Patent
Sugaya et al.

(10) Patent No.: US 7,687,505 B2
(45) Date of Patent: Mar. 30, 2010

(54) USE OF MODIFIED PYRIMIDINE COMPOUNDS TO PROMOTE STEM CELL MIGRATION AND PROLIFERATION

(75) Inventors: Kiminobu Sugaya, Willow Springs, IL (US); Tingyu Qu, Chicago, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 800 days.

(21) Appl. No.: 10/341,683

(22) Filed: Jan. 14, 2003

(65) Prior Publication Data
US 2003/0139410 A1 Jul. 24, 2003

Related U.S. Application Data

(60) Provisional application No. 60/348,473, filed on Jan. 14, 2002, provisional application No. 60/357,783, filed on Feb. 19, 2002, provisional application No. 60/376,257, filed on Apr. 29, 2002, provisional application No. 60/381,138, filed on May 8, 2002, provisional application No. 60/404,361, filed on Aug. 19, 2002, provisional application No. 60/430,381, filed on Dec. 2, 2002.

(51) Int. Cl.
*A61K 31/519* (2006.01)
(52) U.S. Cl. .................................. 514/265.1
(58) Field of Classification Search ................ 514/265.1

See application file for complete search history.

(56) References Cited

U.S. PATENT DOCUMENTS

| | | | |
|---|---|---|---|
| 4,959,368 A | 9/1990 | Awaya | |
| 5,104,650 A | 4/1992 | Ralph et al. | |
| 5,411,883 A | 5/1995 | Boss et al. | |
| 5,589,376 A | 12/1996 | Anderson et al. | |
| 5,750,376 A | 5/1998 | Weiss et al. | |
| 5,753,506 A | 5/1998 | Johe | |
| 5,766,948 A | 6/1998 | Gage et al. | |
| 5,851,832 A | 12/1998 | Weiss et al. | |
| 5,925,567 A | 7/1999 | Kraus et al. | |
| 5,968,829 A | 10/1999 | Carpenter | |

(Continued)

FOREIGN PATENT DOCUMENTS

EP 0 192 783 9/1986

(Continued)

OTHER PUBLICATIONS

Brickman et al., The journal of Biological Chemistry, 1995;270(42):24941-24948.*

(Continued)

*Primary Examiner*—San-ming Hui
(74) *Attorney, Agent, or Firm*—Timothy H. Van Dyke; Beusse Wolter Sanks Mora & Maire

(57) ABSTRACT

This invention provides cells and methods for stimulating proliferation and migration of endogenous and exogenous mammalian stem cells in vivo and in vitro. The invention provides reagents and methods for efficiently proliferating mammalian stem cells in an animal in need thereof and producing stem cells that can be re-introduced into an animal in need thereof to alleviate neurological and corporal disorders.

14 Claims, 4 Drawing Sheets a b

U.S. PATENT DOCUMENTS

| | | | |
|---|---|---|---|
| 5,976,523 A * | 11/1999 | Awaya et al. | 424/85.1 |
| 5,980,885 A | 11/1999 | Weiss et al. | |
| 6,013,521 A | 1/2000 | Gage et al. | |
| 6,020,197 A | 2/2000 | Gage et al. | |
| 6,040,180 A | 3/2000 | Johe | |
| 6,090,624 A | 7/2000 | Greenwood et al. | |
| 6,117,675 A | 9/2000 | Van der Kooy et al. | |
| 6,254,865 B1 | 7/2001 | Freed et al. | |
| 6,284,245 B1 | 9/2001 | Edge | |
| 6,306,575 B1 | 10/2001 | Thomas et al. | |
| 6,368,854 B2 | 4/2002 | Weiss et al. | |
| 6,497,872 B1 | 12/2002 | Weiss et al. | |
| 6,638,501 B1 | 10/2003 | Bjornson et al. | |
| 6,670,397 B1 | 12/2003 | Baranowitz | |
| 6,787,355 B1 | 9/2004 | Miller et al. | |
| 6,808,702 B2 | 10/2004 | Pasricha et al. | |
| 6,824,973 B2 | 11/2004 | Tang et al. | |
| 6,833,269 B2 | 12/2004 | Carpenter | |
| 2001/0038836 A1 | 11/2001 | During et al. | |
| 2002/0091133 A1 | 7/2002 | Taylor | |
| 2002/0142457 A1 | 10/2002 | Umezawa et al. | |
| 2002/0146821 A1 | 10/2002 | Sanchez-Ramos et al. | |
| 2002/0168350 A1 | 11/2002 | Brazelton et al. | |
| 2002/0168765 A1 | 11/2002 | Prockop et al. | |
| 2003/0053992 A1 | 3/2003 | Rader et al. | |
| 2003/0059868 A1 | 3/2003 | Greenwood et al. | |
| 2003/0118566 A1 | 6/2003 | Neuman et al. | |
| 2003/0139410 A1 | 7/2003 | Sugaya et al. | |
| 2003/0148513 A1 | 8/2003 | Sugaya et al. | |
| 2003/0219898 A1 | 11/2003 | Sugaya et al. | |
| 2004/0034049 A1 | 2/2004 | Okawa et al. | |
| 2004/0103448 A1 | 5/2004 | Bjorklund | |
| 2004/0106197 A1 | 6/2004 | Okano et al. | |
| 2005/0169897 A1 | 8/2005 | Snyder et al. | |
| 2005/0181503 A1 | 8/2005 | Goldman et al. | |

FOREIGN PATENT DOCUMENTS

| | | |
|---|---|---|
| EP | 0 305 184 | 3/1989 |
| EP | 0 612 746 | 8/1994 |
| EP | 0 648 495 | 4/1995 |
| JP | 64-040483 | 2/1989 |
| JP | 64-079183 | 3/1989 |
| JP | 1-139572 | 6/1989 |
| JP | 7-90002 | 4/1995 |
| JP | 8-502172 | 3/1996 |
| JP | 8-325268 | 12/1996 |
| JP | 9-507747 | 8/1997 |
| JP | 9-295946 | 11/1997 |
| JP | 9-328435 | 12/1997 |
| JP | 10-504308 | 4/1998 |
| JP | 2001-504123 | 3/2001 |
| JP | 2001-526884 | 12/2001 |
| JP | 2002-500624 | 1/2002 |
| JP | 2002-502858 | 1/2002 |
| JP | 2002-518990 | 7/2002 |
| WO | WO 87/04928 | 8/1987 |
| WO | WO 89/01938 | 3/1989 |
| WO | WO 93/01275 | 1/1993 |
| WO | WO 94/09119 | 4/1994 |
| WO | WO 94/10292 | 5/1994 |
| WO | WO 94/16718 | 8/1994 |
| WO | WO 95/13364 | 5/1995 |
| WO | WO 96/04789 | 2/1996 |
| WO | PCT/CA95/00637 | 5/1996 |
| WO | WO96/15226 | 5/1996 |
| WO | WO 98/22127 | 5/1998 |
| WO | WO 98/32457 | 7/1998 |
| WO | WO 99/11758 | 3/1999 |
| WO | WO 99/32606 | 7/1999 |
| WO | WO 99/40107 | 8/1999 |
| WO | WO 99/43286 | 9/1999 |
| WO | PCT/US99/27613 | 5/2000 |
| WO | WO00/29550 | 5/2000 |
| WO | WO 00/69448 | 11/2000 |
| WO | WO 01/11011 | 2/2001 |
| WO | WO 01/34167 | 5/2001 |
| WO | WO 01/53461 | 7/2001 |
| WO | WO 01/59072 | 8/2001 |
| WO | WO 02/064748 | 8/2002 |
| WO | PCT/US03/01254 | 7/2003 |
| WO | WO03/060085 A2 | 7/2003 |
| WO | WO 2005/009359 A2 | 2/2005 |

OTHER PUBLICATIONS

Fukuyama et al., "A synthesized pyrimidine compound, MS-818, promotes walking function recovery from crush injury of the sciatic nerve through its indirect stimulation of Schwann cells" *Restorative Neurology and Neuroscience* 17 (2000) 9-16.

Yoshikawa et al., "The Effect of MS-818, Newly Synthesized Pyrimidine Compound, on Fracture Repair" *Kobe J. Med. Sci.* 46:265-282 (Dec. 2000).

Itoh et al., "The effect of neurotrophic pyrimidine heterocyclic compounds, MS-818 and MS-430, on the regeneration of injured peripheral nerves" *Restorative Neurology and Neuroscience* 14:265-273 (1999).

Jiang et al., "The effect of MS-818, a pyrimidine compound, on the regeneration of peripheral nerve fibers of mice after a crush injury" *Acta Neuropathol* 90:130-134 (1995).

Yasuhara et al., "The Neurotrophic Pyrimidine Heterocyclic Compound MS-818 Promotes the Angiogenesis Induced by Basic FGF" *Int. J. Clin. Pharm. Res.* XV(5/6) 167-174 (1995).

Koyama et al., "Neurotropic Pyrimidine Heterocyclic Compounds. II. Effects of Novel Neurotropic Pyrimidine Derivatives on Astrocytic Morphological Differentiation" *Biol. Pharm. Bull.* 20(2) 138-141 (1997).

Torigoe et al., "A newly synthesized neurotropic pyrimidine compound, MS-818, may activate migratory Schwann cells in peripheral nerve regeneration" *Brain Research* 787(1998) 337-340.

Watanabe et al., "A Neurotrophic Pyrimidine Compound, MS-818, Enhances EGF-Induced Restoration of Gastric Epithelial Wounds in Vitro" *J. Clin. Gastroenterol* 1988:27(Suppl. 1)S105-S109.

Sugiyama et al., "Accleration by MS-818 of Early Muscle Regeneration and Enhanced Muscle Recovery after Surgical Transection" *Muscle & Nerve* Feb. 2002 218-229.

Daadi et al Generation of tyrosine hydroxylase-producing neurons from precursors of the embryonic and adult forebrain. The Journal of Neuroscience. Jun. 1, 1999, vol. 19, No. 11, pp. 4484-4497.

Murphy et al. Neural Stem Cells. Journal of Investigative Dermatology Symposium Proceedings. Aug. 1997, vol. 2, No. 1, pp. 8-13.

Mazurova et al. New therapeutic approaches for the treatment of Huntington's disease. Acta Medica 2001, vol. 44, No. 4, pp. 119-123.

Memberg et al. Proliferation, differentiation and survival of rat sensory neuron precursors in vitro require specific trophic factors. Molecular and Cellular Neuroscience. Aug. 1995, vol. 6, No. 4, pp. 323-335.

Andrews et al. TNFa potentiates IFN g-induced cell death in oligodendrocyte progenitors. Journal of Neuroscience Research. Dec. 1998, vol. 54, No. 5, pp. 574-583.

Brewer. Regeneration and proliferation of embryonic and adult rat hippocampal neurons in culture. Experimental Neurology. Sep. 1999, vol. 159, No. 1, pp. 237-247.

International Preliminary Examination Report of Nov. 5, 2003 for PCT/US03/01254.

International Preliminary Examination Report of Dec. 23, 2003 for PCT/US03/01014.

International Preliminary Examination Report of Dec. 31, 2003 for PCT/US03/01258.

Pagan, R. et al. Epithelial-mesenchymal transition of cultured rat neonatal hepatocytes is differentially regulated in response to epidermal growth factor and dimethyl sulfoxide. 1997, Hepatology, vol. 25, No. 3, pp. 598-606.

Cheng, C. et al. In vivo proliferation, migration and phenotypic changes of Schwann cells in the presence of myelinated fibers. Neuroscience. Nov. 2002, vol. 115, No. 1, pp. 321-329.
Bayarshaihan, D. et al. Rapid identification of novel chondrocyte-specific gene by RNA differential display. Biochem. And Biophys. Res. Comm. 1995, vol. 220, pp. 449-452.
Sanjo et al. A novel neutrophic pyrimidine compound MS-818 enhances neurotrophic effects of basic fibriblast growth factor. Journal of Neuroscience Research, 1998, vol. 54, pp. 604-612.
Burt et al. Treatment of autoimmune disease by intense immunosuppressive conditioning and autologous hematopoietic stem cell transplantation. Blood, 1998, vol. 92, No. 10, pp. 3505-3514.
Alvarez-Buylla et al., 1997, *J. Neurobiology 33*: 585-601.
Benninger et al., 2000, *Brain Pathol. 10*: 330-341.
Blakemore et al., 1991, *Trends Neurosci. 14*: 323-327.
Blakemore et al., 2000, *Cell Transplant. 9*: 289-294.
Brannen et al., 2000, *Neuroreport 11*: 1123-8.
Carpenter et al., 1999, *Experimental Neurology 158*: 265-278.
Cattaneo et al., 1996, *Mol. Brain Res. 42*: 161-66.
Doetsch et al., 1999, *Cell 97*: 703-16.
Eckenstein et al., 1994, *Biochem. Pharmacol. 47*: 103-110.
Fricker et al., 1999, *J. Neurosci. 19*: 5990-6005.
Frölichsthal-Schoeller et al., 1999, *NeuroReport 10*: 345-351.
Gonzalez et al., 1995, *Brain Res. 701*: 201-226.
Gould et al., 1999, *Science 286*: 548-552.
Hatton et al., 1992, *Glia 5*: 251-258.
Johansson et al., 1999, *Cell 96*: 25-34.
Kurimoto et al., 2001, Neurosci Let. 306: 57-60.
Lundberg et al., 1996, *Exp. Neurol. 139*: 39-53.
Nishida et al., 2000, Invest Ophthalmol Vis Sci 41: 4268-74.
Pundt et al., 1995, *Brain Res. 695*: 25-36.
Qu et al., 2001, *Neuroreport 12*: 1127-32.
Rosser et al., 2000, *Eur. J. Neurosci. 12*: 2405-2413.
Rubio et al., 2000, *Mol. Cell. Neurosci. 16*:1-13.
Svendsen et al., 1998, *J. Neurosci. Methods 85*: 141-152.
Svendsen et al., 1999, *Brain Pathol. 9*: 499-51.
Warfvinge et al., 2001, Exp. Neurol. 169: p. 1-12.
Williams et al., 1996, *J. Comp. Neurol. 370*: 147-158.
Qu et al., (2001), Society for Neuroscience Abstracts, "In vivo differentiation and migration properties of mesenchymal stem cells", vol. 27(1), p. 969; 31st Annual Meeting of the Society for Neuroscience; San Diego, California, USA; Nov. 10-15, 2001.
Qu et al., (2002), Society for Neuroscience Abstracts Viewer and Itinerary Planner, "A seven fold increase in neural stem cell population is induced by pyrimidine derivative MS—818", Abstract No. 825.8, 32nd Annual Meeting of the Society for Neuroscience; Orlando, Florida, USA; Nov. 2-7, 2002.

Ferrari et al., (1998), Muscle regeneration by bone marrow-derived myogenic progenitors, Science 279: 1528.
Gussoni et al., (1999), Dystrophin expression in the mdx mouse restored by stem cell transplantation, Nature 401: 390.
Petersen et al., (1999), Bone marrow as a potential source of hepatic oval cells, Science 284: 1168.
Pereira et al., (1995), Cultured adherent cells from marrow can serve as long-lasting precursor cells for bone, cartilage, and lung in irradiated mice, PNAS 92:4857.
Prockop et al., (1997), Marrow stromal cells as stem cells for nonhematopoietic tissues, Science 276:71.
Pittenger et al., (1999), Multilineage potential of adult human mesenchymal stem cells, Science 284:143.
Kessler PD, (1999), Myoblast cell grafting into heart muscle: cellular biology and potential applications, Annu. Rev. Physiol. 61:219.
Coleman et al., (1996), A clonal study of the reversible inhibition of muscle differentiation by the halogenated thymidine analog 5-bromodeoxyuridine, Developmental Biology, 19:527-548.
Kidson et al., (1990), Effect of Thymidine Analogs on Tyrosinase Activity and mRNA Accumulation in Mouse Melanoma Cells, Experimental Cell Research, 188:36-41.
Kopen et al., (1999), Marrow stromal cells migrate throughout forebrain and cerebellum, and they differentiate into astrocytes after injection into neonatal mouse brains, Proc. Nat'l. Acad. Sci., 96:10711-10716.
Awaya, Akira, et al., "Neurotropic Pyrimidine Heterocyclic Compounds. I. The Newly Synthesized Pyrimidine Compounds Promote Neurite Outgrowth of GOTO and Neuro 2a Neuroblastoma Cell Lines, and Potentiate Nerve Growth Factro (NGF)-Induced Neurite Sprouting of PC 12 Cells," Bio. Pharm. Bull., 1993, 16(3), pp. 248-253.
Noda, Masayuki, et al., "Increase of Nerve Regeneration Capacity by New Neurotrophic Pyrimidine Derivative MS-430," Gen. Pharmac., 1998, vol. 31, No. 5, pp. 821-824.
Ohnishi, Akio, et al., "The Effect of MS-430, a Synthetized Pyrimidine Compound, on regeneration of Nerve Fibers of Rats after Crush Injury," J UOEH, 1995, 17(2), pp. 131-139.
Sager, Ruth, et al., "Pre-Adipocyte Determination either by Insulin or by 5-Azacytidine," Proc. Natl. Acad. Sci., Cell Biology, 1982, vol. 79, pp. 480-484.
Kohyama, Jun, et al., "Brian From Bone: Efficient 'Meta-Differentiation' of Marrow Stroma-Derived Mature Osteoblasts to Neurons with Noggin or A Demethylating Agent," Differentiation, 2001, vol. 68, pp. 235-244.

* cited by examiner

USE OF MODIFIED PYRIMIDINE COMPOUNDS TO PROMOTE STEM CELL MIGRATION AND PROLIFERATION

This application is related to U.S. Provisional Patent Application, Ser. No. 60/348,473, filed Jan. 14, 2002, and Ser. No. 60/357,783, filed Feb. 19, 2002, and Ser. No. 60/376,257, filed Apr. 29, 2002, and Ser. No. 60/381,138, filed May 8, 2002, and Ser. No. 60/404,361, filed Aug. 19, 2002, and Ser. No. 60/430,381, filed Dec. 2, 2002, the disclosures of each of which are expressly incorporated by reference herein.

This invention was made with support from the U.S. Government through the National Institutes of Health, grant no. R03-AG 19874. The government has certain rights in this invention.

BACKGROUND OF THE INVENTION

1. Field of the Invention

This invention relates to methods for stimulating proliferation and migration of mammalian stem cells in vivo and in vitro and cells produced by those methods. In particular, the invention provides reagents and methods for efficiently proliferating stem cells in an animal in need thereof and producing stem cells that can be re-introduced into an animal in need thereof to alleviate neurological and corporal disorders.

2. Background of the Related Art

Stem cells are often defined as self-renewing and multipotent, with the ability to generate diverse types of differentiated cells. As such, they show promise in the treatment of neurological and corporal disorders (also referred to as neurological and corporal "deficits"), or any loss or diminishment of tissue function due to age, disease, trauma or other factor. However, such treatments have faced significant hurdles that have yet to be substantially overcome.

NSCs and Neurological Deficits

Because an important focus of stem cell replacement therapies has been neurological disorders, neural stem cells, and particularly fetal neural stem cells, have been a major research target. During development of the central nervous system (CNS), multipotent neural stem cells (MNSCs), also known as multipotent precursor cells (MPCs), or tissue-specific neural stem cells (NSCs), proliferate, giving rise to transiently dividing progenitor cells that eventually differentiate into the cell types that compose the adult brain, including neurons, astrocytes and oligodendrocytes. NSCs have been isolated from several mammalian species, including mice, rats, pigs and humans. See, e.g., International Application, Publication Nos. WO 93/01275, WO 94/09119, WO 94/10292, WO 94/16718 and Cattaneo et al., 1996, *Mol. Brain Res.* 42: 161-66. NSCs from the embryonic and adult rodent central nervous system (CNS) have been isolated and further propagated in vitro in a variety of culture systems. See, e.g., Frolichsthal-Schoeller et al., 1999, *NeuroReport* 10: 345-351; Doetsch et al., 1999, *Cell* 97: 703-716. NSCs from the human fetal brain have been cultured using serum-free medium supplemented with epidermal growth factor (EGF) and/or basic fibroblast growth factor (bFGF). See, e.g., Svendsen et al., 1998, *J. Neurosci. Meth.* 85: 141-152; Carpenter et al., 1999, *Exp. Neurol.* 158: 265-278. NSCs cultured utilizing these serum-free, mitogen-supplemented methods generally form substantially undifferentiated, clustered aggregates. Upon removal of the mitogen(s) and provision of a substrate, these neural stem cells differentiate into neurons, astrocytes and oligodendrocytes.

While the synaptic connections involved in neural circuits are continuously altered throughout the life of the individual, due to synaptic plasticity and cell death, neurogenesis (the generation of new neurons) was thought to be complete early in the postnatal period. The discovery of MNSCs in the adult brain (see, e.g., Alvarez-Buylla et al., 1997, *J. Neurobiol.* 33: 585-601; Gould et al., 1999, *Science* 286: 548-552) has significantly changed the theory on neurogenesis, as the presence of MNSCs in the adult brain suggests that regeneration of neurons can occur throughout life. Nevertheless, age, physical and biological trauma or neurodegenerative disease-associated loss of brain function, herein referred to as a "neurological deficit," can far outweigh any potential restorative effects due to endogenous neurogenesis. As a result, up-regulated or stimulated proliferation of endogenous MNSCs as well as transplantation of MNSCs are potentially valuable treatments for those suffering from the loss of, or loss of appropriate, brain function due to age, physical and biological trauma or neurodegenerative disease (i.e., a neurological deficit). No such treatments are known in the art.

Due to the advancing average age of the population, and concomitantly increased incidence of neurological deficit that accompanies advancing age, treatment of neurodegenerative diseases has become a major concern. Such diseases, including Alzheimer's disease, Huntington's chorea and Parkinson's disease, have been linked to neuronal degeneration at specific locations in the brain leading to the inability of the brain region to synthesize and release neurotransmitters that are vital to neuronal signaling.

Neurodegeneration also encompasses many conditions and diseases, age-related or not, that result in neuronal loss. These conditions include CNS trauma, such as ischemia (stroke) and epilepsy, as well as diseases that result in neuronal loss, including amyotrophic lateral sclerosis and cerebral palsy.

Many such neurological deficits are localized to particular regions of the brain. Degeneration in a brain region known as the basal ganglia can lead to diseases with varied and different cognitive and motor symptoms, depending on the exact location of the lesion. The basal ganglia consists of many separate regions, including the striatum (which consists of the caudate and putamen), the globus pallidus, the substantia nigra, substantia innominata, ventral pallidum, nucleus basalis of Meynert, ventral tegmental area and the subthalamic nucleus.

Degeneration in the basal ganglia can lead to motor deficits. For example, Huntington's chorea is associated with degeneration of neurons in the striatum, which leads to involuntary jerking movements. Degeneration of a small region called the subthalamic nucleus is associated with violent flinging movements of the extremities in a condition called ballismus, while degeneration in the putamen and globus pallidus are associated with a condition of slow writhing movements or athetosis. In Parkinson's disease, degeneration is seen in another area of the basal ganglia, the substantia nigra par compacta. This area normally sends dopaminergic connections to the dorsal striatum, which are important in regulating movement. Therapy for Parkinson's disease has centered upon restoring dopaminergic activity to this circuit.

Alzheimer's disease patients exhibit a profound cellular degeneration of the forebrain and cerebral cortex. Further, a localized area of the basal ganglia, the nucleus basalis of Meynert, appears to be selectively degenerated. This nucleus normally sends cholinergic projections to the cerebral cortex that are thought to participate in cognitive functions including memory.

The objective of most CNS therapies is to regain the particular chemical function or enzymatic activity lost due to cellular degeneration. Administration of pharmaceutical compositions has been the main treatment for CNS dysfunction though this type of treatment has complications, including the limited ability to transport drugs across the blood-brain barrier, and drug-tolerance acquired by patients to whom these drugs are administered for long periods.

Transplantation of multipotent stem cells may avert the need not only for constant drug administration, but also for complicated drug delivery systems necessitated by the blood-brain barrier. In practice, however, significant limitations have been found in this technique as well. First, cells used for transplantation that carry cell surface molecules of a differentiated cell from a donor can induce an immune reaction in the recipient, a problem that is exacerbated by the physical damage caused by injection of cells directly into the affected area of the brain. In addition, the neural stem cells must be at a developmental stage where they are able to form normal neural connections with neighboring cells.

For these reasons, initial studies on neurotransplantation centered on the use of fetal cells.

Mammalian fetal brain tissue has proven to have reasonable survival characteristics upon immediate transplantation. Increased survival capability of fetal neurons is thought to be due to the reduced susceptibility of fetal neurons to anoxia compared to adult neurons. An additional factor favoring survival of fetal cells is their lack of cell surface markers, whose presence may lead to rejection of grafted tissue from adults. However, although the brain is considered an immunologically privileged site, some rejection of even fetal tissue can occur. Therefore, the ability to use heterologous fetal tissue is limited by tissue rejection and the resulting need for immunosuppressant drug administration.

The use of large quantities of aborted fetal tissue presents other difficulties as well. Fetal CNS tissue is composed of more than one cell type, and thus is not a well-defined tissue source. In addition, it may be unlikely that an adequate and constant supply of fetal tissue would be available for transplantation. For example, in the treatment of MPTP-induced Parkinsonism, tissue from as many as 6 to 8 fetuses can be required for successful implantation into the brain of a single patient. There is also the added problem of the potential for contamination during fetal tissue preparation. Since this tissue may already be infected with a bacteria or virus, expensive diagnostic testing is required for each fetus used. Even comprehensive diagnostic testing might not uncover all infected tissue. For example, there can be no guarantee that a sample is HIV-free, because antibodies to the virus are generally not present until several weeks after infection.

In addition to fetal tissue, there are other potential sources of tissue for neurotransplantation, including cell lines and genetically engineered cell types, but both sources have serious limitations. Cell lines are immortalized cells that are derived, inter alia, by transformation of normal cells with an oncogene or by the culturing of cells in vitro with altered growth characteristics. Moreover, adverse immune response potential, the use of retroviruses to immortalize cells, the potential for the reversion of these cells to an amitotic state, and the lack of response by these cells to normal growth-inhibiting signals make such cell lines sub-optimal for widespread use.

Another approach to neurotransplantation involves the use of genetically engineered cell types or gene therapy. However, there still exists a risk of inducing an immune reaction with these cells. In addition, retrovirus mediated transfer may result in other cellular abnormalities. Also, cell lines produced by retrovirus-mediated gene transfer have been shown to gradually inactivate their transferred genes following transplantation and further may also not achieve normal neuronal connections with the host tissue.

Currently available transplantation approaches suffer from significant drawbacks. The inability in the prior art of the transplant to fully integrate into the host tissue, and the lack of availability of suitable cells in unlimited amounts from a reliable source for grafting are significant limitations of neurotransplantation. Studies utilizing intra-tissue injection of dissociated and partially differentiated NSCs have shown little promise (see, e.g., Benninger et al., 2000, *Brain Pathol.* 10: 330-341; Blakemore et al. 2000, *Cell Transplant* 9: 289-294; Rosser et al., 2000, *Eur. J. Neurosci.* 12: 2405-2413; Rubio et al., 2000, *Mol. Cell Neurosci.* 16: 1-13). The results have generally been poor because, among many considerations, the dissociation of clusters of NSCs is known to cause immediate senescence of NSCs and increase the vulnerability of NSCs in culture. See, e.g., Svendsen et al., 1998, *J. Neurosci. Meth.* 85: 141-152. Further, regardless of adverse immune responses provoked by foreign tissue being introduced into the brain, the trauma caused by the physical introduction of cells directly into the damaged area can induce the recruitment of immune cells by the host that can eliminate the transplanted cells. Thus, significant problems with the use of NSCs to ameliorate neurological deficits remain. As described herein, neurological deficits also include non-brain tissues such as, for example, the eye and spinal cord.

A "corporal deficit" is a disorder caused by a wide variety of diseases and injuries, resulting in trauma, malfunction, degeneration or loss of muscle such as, for example, cardiac muscle due to myocardial infarction. Other examples include malfunction, degeneration or loss of other cells and tissues apart from those discussed in the neurological deficit section above such as, for example, internal organs. For example, liver function can be adversely affected by, among other things, disease (e.g., cirrhosis or hepatitis), trauma or age. The problems described above in using NSCs to remedy neurological deficits of the brain also apply to neurological deficits in other tissues, such as the eye, and corporal deficits.

There exists a need in the art for improved methods for increasing the number of multipotent cells in an animal and thereby increasing the reservoir of remedial capacity conferred by multipotent stem cells in tissues. There exists a need to stimulate proliferation, migration or both proliferation and migration of endogenous and exogenously introduced mammalian multipotent stem cells in vivo as well as mammalian multipotent stem cells in vitro. There exists a need for cells stimulated to proliferate, migrate or both proliferate and migrate, as well as pharmaceutical compositions for treating a neurological deficit or corporal deficit comprising such stimulated cells. Further, there exists a need in the art for methods of administration of such cells stimulated to proliferate, migrate or both proliferate and migrate and pharmaceutical compositions thereof. Still further, there exists a need for methods for treating an animal having a neurological or corporal deficit.

SUMMARY OF THE INVENTION

This invention provides methods for stimulating proliferation, migration or both proliferation and migration of mammalian stem cells in vivo and in vitro and cells produced by those methods. In particular, the invention provides reagents and methods for efficiently proliferating stem cells in an animal in need thereof and producing stem cells that can be re-introduced into an animal in need thereof to alleviate neurological disorders.

In a first aspect, the invention provides a method of stimulating proliferation, migration or both proliferation and migration of endogenous and exogenous mammalian stem cells in vivo. In one embodiment, the method comprises the step of introducing to a mammal an effective amount of a pyrimidine derivative of:

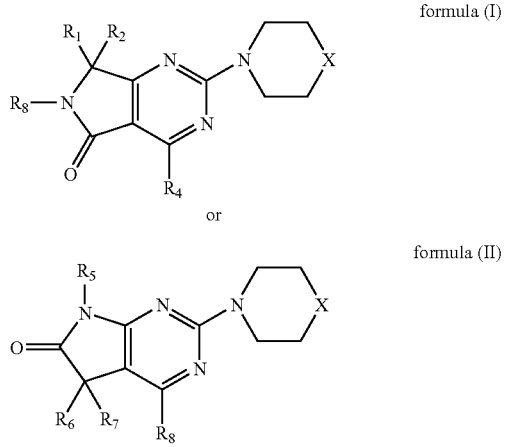

where $R_1$ to $R_8$ independently represent a hydrogen atom, a lower alkyl group, $CH_3OCH_2CH_2$—, $CH_2CONH_2$, —$COCH_3$, —$COC_2H_5$ or —$CH_2OCOC_2H_5$; and X is NH, N—$CH_3$, N—$C_2H_5$, N-ph, N—$COOC_2H_5$, N—$SO_2CH_3$, $CH_2$, $CHCH_3$, $CHC_2H_5$, —O— or —S— in which ph stands for a phenyl group; or a pharmaceutically acceptable salt thereof.

In another aspect, the invention provides a method of stimulating proliferation, migration or both proliferation and migration of exogenous mammalian stem cells in vivo to a mammal that has had more developmentally potent cells or the autologous stem cells or the non-autologous stem cells administered thereto. In one embodiment, the method comprises the step of introducing to a mammal an effective amount of the pyrimidine derivative of formulae (I) or (II) above or a pharmaceutically acceptable salt thereof.

In another aspect, the invention provides a method of stimulating proliferation, migration or both proliferation and migration of endogenous mammalian stem cells in vitro. In one embodiment, the method comprises the step of contacting a mammalian stem cell with an effective amount of the pyrimidine derivative of formulae (I) or (II) above or a pharmaceutically acceptable salt thereof.

In another aspect, the invention provides a method for treating an animal with a neurological or corporal deficit. In one embodiment, the method comprises the step of administering an effective amount of the pyrimidine derivative of formulae (I) or (II) above, or a pharmaceutically acceptable salt thereof, wherein the endogenous stem cell population is stimulated to proliferate and migrate to an area of tissue damage, differentiate in a tissue-specific manner and function in a manner that reduces the neurological or corporal deficit. In certain embodiments the inventive methods further comprise the step of administering more developmentally potent cells, wherein the more developmentally potent cells are stimulated to proliferate and migrate to an area of tissue damage, differentiate in a tissue-specific manner and function in a manner that reduces the neurological or corporal deficit. In related embodiments, the inventive method comprises administering autologous or non-autologous stem cells, wherein the autologous or non-autologous stem cells are stimulated to proliferate and migrate to an area of tissue damage, differentiate in a tissue-specific manner and function in a manner that reduces the neurological or corporal deficit. In further related embodiments, the more developmentally potent cells or the autologous stem cells or the non-autologous stem cells administered with the pyrimidine derivative form a cluster of two or more cells. In further related embodiments, the more developmentally potent cells or the autologous stem cells or the non-autologous stem cells are derived from a tissue or tissue-specific stem cell. In other embodiments, the stem cell is a hematopoietic stem cell, a neural stem cell, an epithelial stem cell, an epidermal stem cell, a retinal stem cell, an adipose stem cell or a mesenchymal stem cell, any of which can be obtained from any tissue containing stem cells including but not limited to zygote, blastocyst, embryo, fetus, infant juvenile or adult, and optionally, a human species of any of the preceding embodiments, whether naturally occurring or engineered. In certain embodiments, the cluster of two or more of the more developmentally potent cells or the autologous stem cells or the non-autologous stem cells comprises less than about 50 percent redifferentiated cells, or more preferably less than about 25 percent redifferentiated cells, or even more preferably less than about 10 percent redifferentiated cells, or even more preferably less than about 5 percent redifferentiated cells, or even more preferably less than about 1 percent redifferentiated cells. In related embodiments, the more developmentally potent cells or the autologous stem cells or the non-autologous stem cells, in the form of a cluster of two or more cells in other related embodiments, are administered by injecting the more developmentally potent cells with a syringe, inserting the more developmentally potent cells or the autologous stem cells or the non-autologous stem cells with a catheter or surgically implanting the said cells. In other, further related embodiments, the more developmentally potent cells or the autologous stem cells or the non-autologous stem cells are injected with a syringe, inserted with a catheter or surgically implanted either to a body cavity that is fluidly-connected to the area of neurological or corporal deficit or to the area of neurological or corporal deficit. In embodiments relating to neurological or corporal deficits, the neurological deficit is optionally caused by a neurodegenerative disease, a traumatic injury, a neurotoxic injury, ischemia, a developmental disorder, a disorder affecting vision, an injury or disease of the spinal cord, a demyelinating disease, an autoimmune disease, an infection, or an inflammatory disease and the corporal deficit is optionally caused by corporal disease, disorder, injury, trauma, malfunction, degeneration or loss In certain embodiments the pyrimidine derivative of formula (I) is MS-818, or 2-piperadino-6-methyl-5-oxo-5, 6-dihydro(7H) pyrrolo[2,3-d]pyrimidine maleate (the $C_4H_4O_4$ maleate salt), as disclosed in U.S. Pat. No. 4,959,368, incorporated by reference herein. In certain in vivo embodiments, the pyrimidine derivatives of formulae (I) and (II) is administered at a concentration of between about 0.01 mg/kg/day to 50 mg/kg/day, more preferably between about 0.1 mg/kg/day to 10 mg/kg/day, even more preferably between about 1 mg/kg/day to 5 mg/kg/day, and even more preferably about 3 mg/kg/day. In these embodiments, the pyrimidine derivatives of formulae (I) and (II) is administered for between about 1 and 60 days, or more preferably between about 1 and 30 days, or more preferably between about 1 and 15 days, or even more preferably between about 1 and 10 days, or more preferably between about 2 and 7 days, or even more preferably about 5 days. In certain others of these embodiments, the methods further comprise the step of administering a growth factor. In certain embodiments, the growth factor comprises fibroblast growth factor, epidermal growth factor or a combination thereof.

In certain in vitro embodiments, the stem cell culture is contacted with the pyrimidine derivative of formulae (I) or (II) in an effective amount, or a concentration of between about 50 nM to 1 mM, or more preferably between about 500 nM to 500 µM, or even more preferably between about 1 µM to 100 µM, or more preferably between about 5 µM to 75 µM and even more preferably about 50 µM. In these embodiments, the stem cell culture is contacted with pyrimidine derivatives of formulae (I) and (II) for an effective period, or between about 1 and 60 days, or more preferably between about 1 and 30 days, or more preferably between about 1 and 15 days, or even more preferably between about 1 and 10 days, or more preferably between about 2 and 7 days, or even more preferably about 5 days. In certain others of these embodiments, the methods further comprise the step of contacting the cell culture with a growth factor. In certain embodiments, the growth factor comprises fibroblast growth factor, epidermal growth factor or a combination thereof. In certain others of these embodiments, the methods further comprise contacting the stem cell culture with heparin.

In another aspect, the invention provides cells stimulated for proliferation, migration or both proliferation and migration produced according to the methods of the invention. In another aspect, the invention provides a pharmaceutical composition for treating a neurological or corporal deficit comprising the cells stimulated for proliferation, migration or both proliferation and migration produced according to the methods of the invention. In certain embodiments, the pharmaceutical composition further comprises a pharmaceutically acceptable carrier.

Thus, the invention advantageously provides methods of stimulating proliferation and migration of mammalian stem cells in vivo and in vitro, cells produced by those methods, pharmaceutical compositions to treat neurological and corporal deficits, and methods of administering the cells and pharmaceutical compositions of the invention.

Specific embodiments of the present invention will become evident from the following more detailed description of certain preferred embodiments and the claims.

DETAILED DESCRIPTION OF PREFERRED EMBODIMENTS

Figure 1:
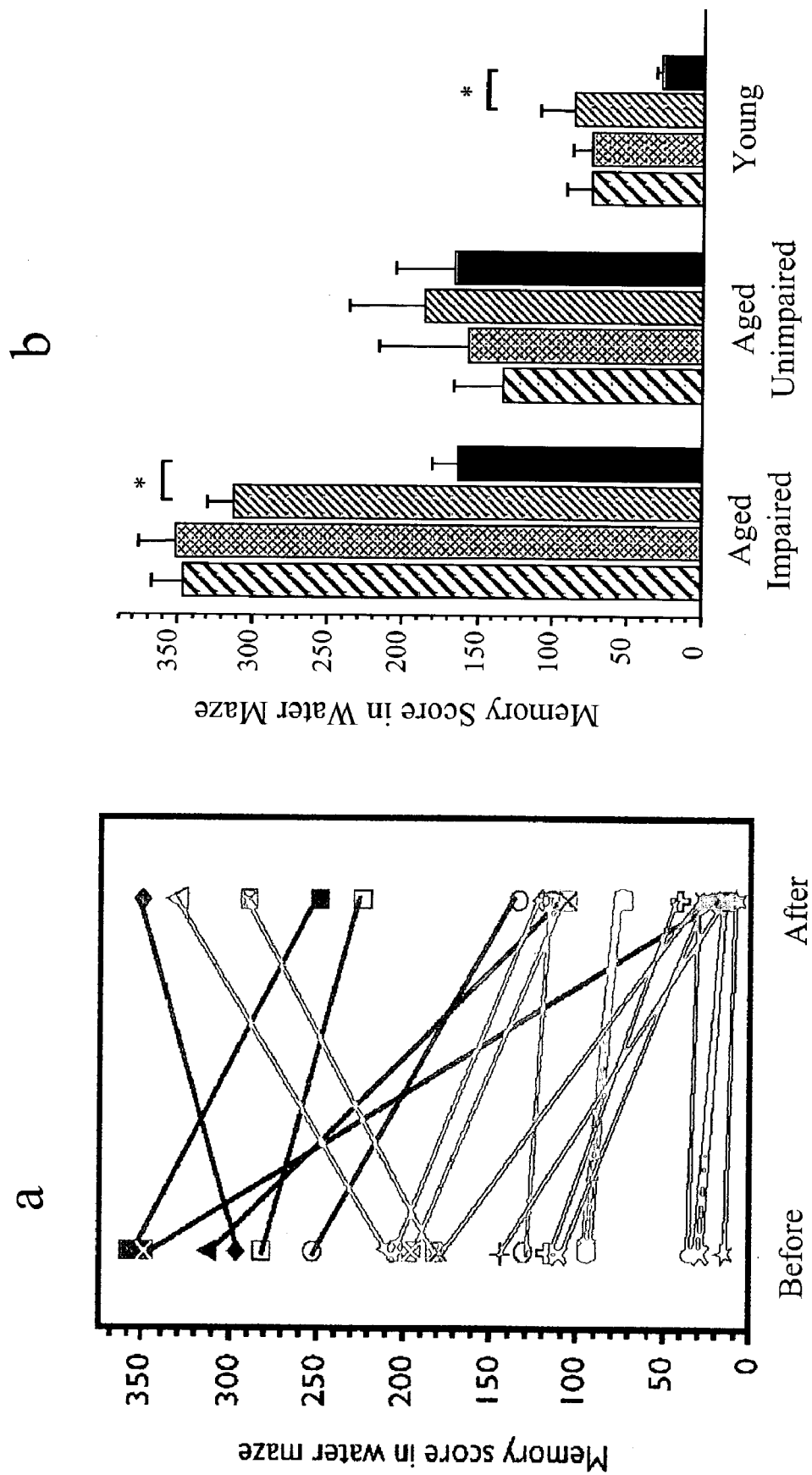
FIG. 1 shows the effect of transplantation of MNSC according to the methods of co-owned and co-pending U.S. patent application, entitled "Novel Mammalian Multipotent Stem Cells and Compositions, Methods of Preparation and Methods of Administration Thereof," (Ser. No. 10/345,126, filed Jan. 14, 2003) on memory score in the Morris water maze test. (a) Individual memory score before and after transplantation shows improvement in the majority of the animals. Blue: Aged memory impaired animals, Green: Aged memory unimpaired animals, Red: Matured animals. (b) Mean of memory score in each animal group before (n arrow striped bar) and after (black bar) SC transplantation shows a significant improvement in aged memory impaired and young animals. The animals that received vehicle injection do not show significant difference in memory score between before (wide striped bar) and after (hatched) the injection. The methods of the instant invention can act to increase the number of such exogenously transplanted cells in vivo, as well as enhance their number while being treated according to the methods of said co-owned and co-pending application. Further, the methods of the instant invention can increase the abundance of the endogenous NSC population.

This invention provides methods for stimulating proliferation, migration or proliferation and migration of endogenous and exogenous mammalian stem cells in vivo. The invention also provides methods for stimulating proliferation, migration or proliferation and migration of mammalian stem cells in vitro. The method further provides cells produced by the aforementioned methods. More generally, the invention provides reagents and methods for efficiently proliferating mammalian stem cells in an animal in need thereof and producing stem cells that can be re-introduced into an animal in need thereof to alleviate neurological and corporal disorders.

As used herein, the terms "multipotent neural stem cells (MNSCs)," "neural stem cells (NSCs)," and "multipotent precursor cells (MPCs)" refer to undifferentiated, multipotent cells of the CNS. Such terms are commonly used in the scientific literature. MNSCs can differentiate into tissue-specific cell types, for example astrocytes, oligodendrocytes, and neurons when transplanted in the brain. The multipotent cells of the invention are distinguished from natural NSCs by their stimulation for proliferation, migration or both proliferation and migration due to treatment by the methods of the invention.

As used herein, a "less developmentally potent cell" is a cell that is capable of limited multi-lineage differentiation or capable of single-lineage, tissue-specific differentiation, for example, an untreated mesenchymal stem cell can differentiate into, inter alia, osteocytes and chrondrocytes, i.e., cells of mesenchymal lineage but has only limited ability to differentiate into cells of other lineages (e.g., neural lineage.).

As used herein, a "more developmentally potent cell" is a cell that is readily capable of differentiating into a greater variety of cell types than its corresponding less developmentally potent cell. For example, a mesenchymal stem cell can readily differentiate into osteocytes and chrondrocytes but has only limited ability to differentiate into neural or retinal lineage cells (i.e., it is a less developmentally potent cell in this context). Mesenchymal stem cells treated according to the methods of the above-referenced co-owned and co-pending U.S. patent application become more developmentally potent because they can readily differentiate into, for example, mesenchymal-lineage and neural-lineage cell types; the plasticity of the cells is increased when treated according to the methods of the invention.

"More developmentally potent cell" and "less developmentally potent cell" as used herein are fully disclosed and claimed in co-owned and co-pending U.S. patent application entitled "Novel Mammalian Multipotent Stem Cells and Compositions, Methods of Preparation and Methods of Administration Thereof," Ser. No. 10/345,126, filed Jan. 14, 2003, or "App. 1."

As used herein, "multipotent stem cells" or "MSCs" refer to the cells prepared according to the methods disclosed herein and in co-owned and co-pending U.S. patent application entitled "Novel Mammalian Multipotent Stem Cells and Compositions, Methods of Preparation and Methods of Administration Thereof," Ser. No. 10/345,126, filed Jan. 14, 2003, or "App. 1" and co-owned and co-pending U.S. patent application entitled "Novel Mammalian Multipotent Neural Stem Cells and Compositions, Methods of Preparation and Methods of Administration Thereof," Ser. No. 10/345,126, filed Jan. 14, 2003, or "App. 2." Each application is incorporated herein by reference in their entirety.

As used herein, the term "cluster" refers to a group of two or more non-terminally differentiated cells. A cluster can comprise the progeny of a single multipotent stem cell or small cluster of primary cells.

As used herein, the terms "effective amount" and "therapeutically effective amount" each refer to the amount of reagent used to support or produce the desired activity. In the case of the cells stimulated for proliferation, migration or both proliferation and migration prepared and delivered according to the invention, an effective amount is an amount necessary to support or produce an observable level of one or more biological activities of MSC as set forth herein. Regarding pyrimidine derivatives, an effective amount can be between about 0.01 mg/kg/day to 50 mg/kg/day, more preferably between about 0.1 mg/kg/day to 10 mg/kg/day, even more preferably between about 1 mg/kg/day to 5 mg/kg/day, and even more preferably about 3 mg/kg/day.

An "effective period" as used herein refers to the time period necessary for the reagents and cells of the invention to accomplish their specified activities. For example, cells of the invention can be contacted with a pyrimidine derivative for an effective period to make them more developmentally potent. An effective period for contact with a pyrimidine derivatives can be, for example, between about 1 and 60 days, or more preferably between about 1 and 30 days, or more preferably between about 1 and 15 days, or even more preferably between about 1 and 10 days, or more preferably between about 2 and 7 days, or even more preferably about 5 days.

The term "pharmaceutically acceptable carrier" or "physiologically acceptable carrier" as used herein refers to one or more formulation materials suitable for accomplishing or enhancing the successful delivery of the pharmaceutical composition of stimulated stem cells prepared and delivered according to the invention.

As disclosed in further detail herein, the inventive methods provide for introducing pyrimidine derivatives of formulae (I) or (II),

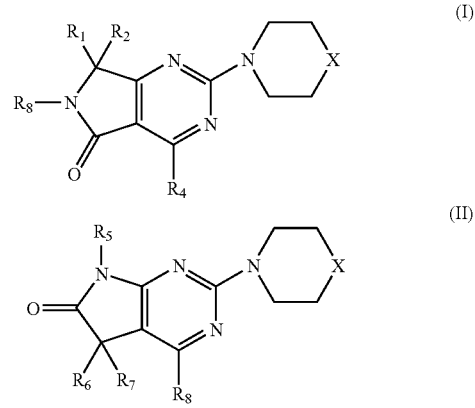

where $R_1$ to $R_8$ independently represent a hydrogen atom, a lower alkyl group, $CH_3OCH_2CH_2$—, $CH_2CONH_2$, —$COCH_3$, —$COC_2H_5$ or —$CH_2OCOC_2H_5$; and X is NH, N—$CH_3$, N—$C_2H_5$, N-ph, N—$COOC_2H_5$N—$SO_2CH_3$, $CH_2$, $CHCH_3$, $CHC_2H_5$, —O— or —S— in which ph stands for a phenyl group; or a pharmaceutically acceptable salt thereof, to a mammal in an amount effective to stimulate proliferation, migration or both proliferation and migration of endogenous multipotent stem cells in vivo. Endogenous multipotent stem cells can be of varied origin, inter alia, stem cells of hematopoietic, neural, mesenchymal, epithelial, epidermal, adipose and retinal origin, and administration of the pyrimidine derivatives can be localized to a particular tissue.

The invention also provides methods for introducing pyrimidine derivatives, or pharmaceutically suitable salts thereof, to a mammal in an amount effective to stimulate proliferation, migration or both proliferation and migration, in vivo, of exogenous multipotent stem cells introduced to the mammal before, after or concurrently with the pyrimidine derivative. Further, a rest period between the introduction of the pyrimidine derivative and the multipotent stem cells can be implemented as necessary to minimize any trauma caused by their administration. The exogenously introduced multipotent stem cells can be prepared according to the methods described in App. 1 or App. 2, and as set forth below.

Both the pyrimidine derivatives and the exogenous multipotent stem cells can be administered by injection with a syringe, insertion with a catheter or surgical implantation. The pyrimidine derivatives can be administered at the site of neurological or corporal deficit, systemically (e.g., intravenously), or in the case of neurological deficits of the brain, spinal cord or any tissues accessible by cerebral spinal fluid (CSF), in a brain ventricle. The exogenous multipotent stem cells can be administered at the site of neurological or corporal deficit, systemically (e.g., intravenously), or in the case of neurological deficits of the brain, spinal cord or any tissues accessible by cerebral spinal fluid (CSF), in a brain ventricle.

In another in vivo embodiment, the invention provides a method for treating an animal with a neurological or corporal deficit. In one embodiment, the method can comprise administering an effective amount of a pyrimidine derivative or pharmaceutically acceptable salt thereof such that the endogenous stem cell population is stimulated to proliferate and migrate to an area of tissue damage, differentiate in a tissue-specific manner and function in a manner that reduces the neurological or corporal deficit. In other embodiments, the inventive method further comprises the step of administering multipotent stem cells of App. 1 or App. 2, referenced above, wherein the exogenous multipotent stem cells are stimulated to proliferate and migrate to an area of tissue damage, differentiate in a tissue-specific manner and function in a manner that reduces the neurological or corporal deficit. Similarly, in related embodiments, the inventive method can comprises administering autologous or non-autologous stem cells instead of administering the multipotent stem cells of App. 1 or App. 2, wherein the autologous or non-autologous stem cells are stimulated to proliferate and migrate to an area of tissue damage, differentiate in a tissue-specific manner and function in a manner that reduces the neurological or corporal deficit. As an example, tissue-specific stem cells can be isolated from the eventual recipient or another source, and administered with the pyrimidine derivative. The isolated cells can be treated in vitro with the pyrimidine derivative or be left untreated with the pyrimidine derivative. When the autologous or non-autologous stem cells are administered to the human or animal with a neurological or corporal deficit, the cells differentiate in a tissue-specific manner according to their natural potency. For example, hematopoietic stem cells have some natural, limited capacity to differentiate into certain skin cells. According to this embodiment, hematopoietic stem cells could be isolated from the recipient of another source and treated before, concurrently, or after administration to the recipient with a pyrimidine derivative. Such cells are stimulated for proliferation, migration or both proliferation and migration, and differentiate according to the environmental signals they (1) actually encounter and (2) are capable of naturally responding to. Thus, hematopoietic stem cells administered to a skin wound with pyrimidine derivative proliferate and migrate due to the exposure to the pyrimidine derivative and differentiate according to the environmental signals they encounter in the wound and are capable of responding to. Immunosuppressant drugs can be used to suppress any immunorejection of non-autologous cells. Similarly, mesenchymal stem cells can be isolated from an animal in need of additional mesenchymal stem cells. Limited numbers of cells can be isolated and treated with pyrimidine derivatives according to the methods of the invention. Such cells can be stimulated to proliferation, migration or both due to exposure to the pyrimidine derivative. Large numbers of cells can be propagated in vitro and reintroduced to the donor or other, non-autologous recipient.

The multipotent stem cells can be administered in the form a cluster of two or more cells. The multipotent stem cells can be derived from a tissue or tissue-specific stem cell, for example, a hematopoietic stem cell, a neural stem cell, an epithelial stem cell, an epidermal stem cell, a retinal stem cell, an adipose stem cell and a mesenchymal stem cell, any of which can be obtained from any tissue containing stem cells including but not limited to zygote, blastocyst, embryo, fetus, infant juvenile or adult, and optionally, a human species of any of the preceding embodiments, whether naturally occurring or engineered.

When utilizing "more developmentally potent" multipotent stem cells or autologous stem cells or non-autologous stem cells in a cluster of two or more cells, the cluster of multipotent stem cells can comprise less than about 50 percent redifferentiated cells, or more preferably less than about 25 percent redifferentiated cells, or even more preferably less than about 10 percent redifferentiated cells, or even more preferably less than about 5 percent redifferentiated cells, or even more preferably less than about 1 percent redifferentiated cells. "Redifferentiated cells" as used herein, refers to cells that have terminally differentiated during the performance of the methods herein prior to migration, differentiation and incorporation into host tissue to.

Similar to other embodiments described above, the multipotent stem cells, optionally in cluster form, are administered by injecting with a syringe, inserting with a catheter or implanting surgically. The multipotent stem cells can be administered at the site of neurological or corporal deficit, systemically (e.g., intravenously), or in the case of neurological deficits of the brain, spinal cord or any tissues accessible by cerebral spinal fluid (CSF), in a brain ventricle. In other words, the cells can be implanted to a body cavity that is fluidly-connected to the area of neurological or corporal deficit or directly to the area of neurological or corporal deficit. The neurological deficit is optionally caused by a neurodegenerative disease, a traumatic injury, a neurotoxic injury, ischemia, a developmental disorder, a disorder affecting vision, an injury or disease of the spinal cord, a demyelinating disease, an autoimmune disease, an infection, or an inflammatory disease and the corporal deficit is optionally caused by corporal disease, disorder, injury, trauma, malfunction, degeneration or loss.

In the methods relating to the in vivo stimulation of proliferation and migration of endogenous and exogenous mammalian stem cells, an effective amount of pyrimidine derivatives is administered. An effective amount can be, for example, a concentration effective to accomplish aforementioned effects. Non-limiting, exemplary concentrations can be between about 0.01 mg/kg/day to 50 mg/kg/day, more preferably between about 0.1 mg/kg/day to 10 mg/kg/day, even more preferably between about 1 mg/kg/day to 5 mg/kg/ day, and even more preferably about 3 mg/kg/day. The pyrimidine derivatives can be administered as necessary to elicit the stimulatory effects, an effective period, which can be, for example, between about 1 and 60 days, or more preferably between about 1 and 30 days, or more preferably between about 1 and 15 days, or even more preferably between about 1 and 10 days, or more preferably between about 2 and 7 days, or even more preferably about 5 days.

The in vivo methods of the invention can further comprise the administration of a growth factor, including, for example, fibroblast growth factor (FGF), epidermal growth factor (EGF) or a combination thereof.

The invention also provides methods of stimulating proliferation, migration or both proliferation and migration of mammalian stem cells in vitro. In one embodiment, the method comprises the step of contacting a mammalian stem cell or in vitro culture thereof with an effective amount of the pyrimidine derivative of formulae (I) or (II) above or a pharmaceutically acceptable salt thereof. The stem cell culture can be contacted with the pyrimidine derivative at a concentration effective to produce the stimulatory effect. For example, a concentration of between about 50 nM to 1 mM can be used, or more preferably between about 500 nM to 500 µM, or even more preferably between about 1 µM to 100 µM, or more preferably between about 5 µM to 75 µM and even more preferably about 50 µM. As with in vivo embodiments, the stem cell culture can be contacted with pyrimidine derivatives for an effective period, which can be, for example, between about 1 and 60 days, or more preferably between about 1 and 30 days, or more preferably between about 1 and 15 days, or even more preferably between about 1 and 10 days, or more preferably between about 2 and 7 days, or even more preferably about 5 days. Also similar to the in vivo embodiments, the cell cultures can be contacted with a growth factor, for example, FGF, EGF or a combination thereof. A growth factor, as defined herein, refers to a protein, peptide or other molecule having a growth, proliferative, or trophic effect on the cells (whether "more" or "less" developmentally potent as defined herein) or progeny thereof. Growth factors used for inducing proliferation include any trophic factor that allows more or less developmentally potent cells to proliferate, including any molecule that binds to a receptor on the surface of the cell to exert a trophic, or growth-inducing effect on the cell. Exemplary proliferation-inducing growth factors include epidermal growth factor (EGF), amphiregulin, acidic fibroblast growth factor (aFGF or FGF-1), basic fibroblast growth factor (bFGF or FGF-2), transforming growth factor alpha (TGFα), and combinations thereof. Preferred proliferation-inducing growth factors include EGF and FGF or a combination thereof. Growth factors are usually added to the culture medium at concentrations of between about 1 fg/mL to 1 mg/mL. Concentrations between about 1 to 100 ng/mL are usually sufficient. Simple titration experiments routine in the art are used to determine the optimal concentration of a particular growth factor for a particular cell culture (see, e.g., Cutroneo et al., 2000, *Wound Repair Regen*, 8: 494-502). The method can, in certain embodiments, further comprise contacting the multipotent stem cell culture with heparin.

The invention also provides cells that are treated according to the methods of the invention and are thereby stimulated to proliferate, migrate or both proliferate and migrate in vivo or in vitro. These cells can be used as an active ingredient in a pharmaceutical composition for treating a neurological deficit or corporal deficit. In certain embodiments, the pharmaceutical composition further comprises a pharmaceutically acceptable carrier as described below.

Pharmaceutical compositions optimally comprise a therapeutically effective amount of the stimulated cells of the invention in admixture with a pharmaceutically or physiologically acceptable formulation agent selected for suitability with the mode of administration. Acceptable formulation materials preferably are nontoxic to the stimulated cells and the recipients at the dosages and concentrations employed.

The pharmaceutical compositions of the invention may contain formulation materials for modifying, maintaining, or preserving, for example, pH, osmolarity, viscosity, clarity, color, isotonicity, odor, sterility, stability, rate of dissolution or release, adsorption, or penetration of the composition, as well as proliferation, migration and differentiation capacity of the stimulated cells of the invention. Suitable formulation materials include, but are not limited to, amino acids (such as glycine, glutamine, asparagine, arginine, or lysine), antimicrobial compounds, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; trimethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See REMINGTON'S PHARMACEUTICAL SCIENCES (18th Ed., A. R. Gennaro, ed., Mack Publishing Company 1990).

The primary vehicle or carrier in a pharmaceutical composition may be either aqueous or non-aqueous in nature. For example, a suitable vehicle or carrier for injection may be water, physiological saline solution, or artificial cerebrospinal fluid. Optimal pharmaceutical compositions will be determined by a skilled artisan depending upon, for example, the intended route of administration, delivery format, desired dosage and recipient tissue. See, e.g., REMINGTON'S PHARMACEUTICAL SCIENCES, supra. Such compositions may influence the physical state, stability, and effectiveness of the composition.

Examples of the pharmaceutically acceptable salts of the compounds of formulae (I) and (II) include hydrochlorides, hydrobromides, sulfates, bisulfites, phosphates, acidic phosphates, acetates, maleates, fumarates, succinates, lactates, tartrates, benzoates, citrates, gluconates, glucanates, methanesulfonates, p-toluenesulfonates and naphthalene-sulfonates which are formed from acids capable of forming pharmaceutically acceptable anion-containing nontoxic acid addition salts, hydrates thereof, and quaternary ammonium (or amine) salts or hydrates thereof. In a preferred embodiments the pyrimidine derivative of formula (I) is 2-piperadino-6-methyl-5-oxo-5,6-dihydro(7H)pyrrolo[2,3-d]pyrimidine maleate (the $C_4H_4O_4$ maleate salt), also known as MS-818 (see, for example, Sanyo et al., 1998, *J. Neurosci Res.* 54: 604-612).

Thus, the invention advantageously provides methods of stimulating proliferation and migration of mammalian stem cells in vivo and in vitro, cells produced by those methods, pharmaceutical compositions to treat neurological and corporal deficits, and methods of administering the cells and pharmaceutical compositions of the invention.

Cells can be obtained in any way known in the art and from any tissue, for example, from donor tissue by dissociation of individual cells from the connecting extracellular matrix of the tissue or from commercial sources of NSCs (e.g., BioWhittaker, Walkersville, Md., CC-2599). Tissue from brain can removed using sterile procedures, and the cells can be dissociated using any method known in the art including treatment with enzymes such as trypsin, collagenase and the like, or by using physical methods of dissociation such as mincing or treatment with a blunt instrument. Dissociation of neural cells can be carried out in tissue culture medium; in a preferred embodiment, the medium for dissociation of juvenile and adult cells is low calcium artificial cerebral spinal fluid (aCSF) having a formula identical to aCSF (124 mM NaCl, 5 mM KCl, 1.3 mM $MgCl_2$, 2 mM $CaCl_2$, 26 mM $NaHCO_3$, and 10 mM D-glucose) except that $MgCl_2$ is present at a concentration of 3.2 mM and $CaCl_2$ at a concentration of 0.1 mM. Dissociated cells are centrifuged at low speed, between 200 and 2000 rpm, usually between 400 and 800 rpm, the suspension medium is aspirated, and the cells are then resuspended in culture medium. Suspension cultures are preferred if large numbers of undifferentiated neural stem cell progeny are desired. Cell suspensions are seeded in any receptacle capable of sustaining cells, preferably culture plates or roller bottles that inhibit contact-dependent stem cell differentiation, including uncoated flask or a flask that has been treated to repel the cells.

While isolation from brain tissue is generally feasible for preparation of exogenous multipotent cells to be administered with the pyrimidine derivative according to the methods of the instant invention, stem cells from bone marrow (e.g., mesenchymal stem cells) are a particularly good source of cells for generating multipotent stem cells of App. 1, because isolation techniques are well established in the art having been used for decades in immune disorder bone marrow transplants. Further, the methods of the instant invention can then be carried out with autologous cells, thus alleviating any concerns over immunological rejection. Thus, a patient's own mesenchymal stem cells can be isolated, treated according to the methods of App. 1 and readministered where necessary. In contrast, autologous transplants using a neural cell source, while certainly not impossible, are not as feasible as, for example, mesenchymal cells.

Growth of multipotent stem cells under the above culture conditions induces or permits these cells to form undifferentiated cell clusters. These clusters are optimally grown at a density of approximately 50 clusters per T75 flask in 20 mL of the growth medium consisting of, for example, DMEM/HAMS F12 (at about 3:1; Gibco, BRL, Burlington, ON), supplemented with an antibiotic-antimycotic mixture (1:100, penicillin G, streptomycin sulfate, amphotericin B; Gibco), B27 (1:50, GIBCO), human recombinant FGF-2 and EGF (20 ng/ml each, R&D Systems, Minneapolis, Minn.) and heparin (5 μg/mL, Sigma, St. Louis, Mo.). The cultures are kept in a $CO_2$ incubator (about 5% $CO_2$) at 37° C. To facilitate optimal growth conditions, clusters of two or more cells are sectioned into quarters approximately every 14 days and fed by replacing 50% of the medium approximately every 4-5 days. These conditions permit rapid and continual growth of MSCs that can be expanded indefinitely while retaining their multipotent character. As with most eukaryotic cells, conditions for culturing should be as close as possible to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C. Multipotent neural stem cells (MNSCs) prepared and maintained as disclosed herein continue to exhibit multipotent character after more than three years of serum-free propagation. Treatment with pyrimidine derivative according to the methods of the invention then transform these cells into the cells of the invention, cells specially stimulated for proliferation, migration or both. If in vitro differentiation is desired, the cells can be replated in culture dishes in, for example, serum-free basal medium Eagle (BME), which contains Earle's salt and L-glutamine. The cells can be cultured for about 5 days in the absence of FGF-2, EGF or other extrinsic differentiation factors. When induced to differentiate in this way, these cultured MNSCs exhibit characteristic morphologies of neurons or astrocytes when immunohistochemically stained with b-III tubulin (a neuronal cell marker) or glial fibrillary acidic protein (GFAP, an astrocyte marker).

MSCs prepared according to the methods of Apps. 1 or 2 and utilized in this invention that are proliferated in serum-free media are grown in the presence of a substituted deoxyuridine. Examples include a halo-deoxyuridine such as bromodeoxyuridine (BrdU) or iododeoxyuridine (IrdU), or an alkyl-substituted deoxyuridine such as a methyldeoxyuridine prior to transplantation into a host. The growth medium used to generate MSCs according to Apps. 1 and 2 for use in the present invention comprises the components of the long-term propagation media, but also contains an effective amount of substituted deoxyuridine, for example, concentrations between about 10 nanomolar and 100 micromolar, more preferably between about 2 and 50 micromolar, and more preferably about 10 micromolar bromodeoxyuridine. Pre-transplantation propagation can extend for an effective period, for example, between about 1 and 10 days, more preferably between about 1 and 5 days and more preferably between about 2 and 3 days.

MSCs prepared according to the methods of Apps. 1 and 2 can be administered according to the instant invention to an animal with abnormal or degenerative symptoms obtained in any manner, including those obtained as a result of age, physical or biological trauma, or neurodegenerative disease and the like, or animal models created by man using recombinant genetic techniques, such as transgenic and "gene knockout" animals.

Recipients of the MSCs and pyrimidine derivatives according to the methods of the invention can be immunosuppressed, either through the use of immunosuppressive drugs such as cyclosporin, or through local immunosuppression strategies employing locally applied immunosuppressants, but such immunosuppression need not necessarily be a prerequisite in certain immunoprivileged tissues such as, for example, brain and eye tissues or in the case of autologous transplantation. In certain embodiments, the delivery method of the invention can cause less localized tissue damage to the site of cell damage or malfunction than existing methods of delivery.

MSCs of Apps. 1 and 2 and used herein can be prepared from the recipient's own tissue. In such instances, the progeny of the more developmentally potent cells can be generated from dissociated or isolated tissue and proliferated in vitro using the methods described in App. 1, App. 2, and herein. In the case of mesenchymal stem cells (MeSCs), progeny can be generated from MeSCs isolated from, for example, bone marrow. Upon suitable expansion of cell numbers, the stem cells of Apps. 1 or 2 can be treated and administered according to the instant invention into the recipient's affected tissue.

It is well recognized in the art that transplantation of tissue into the CNS offers the potential for treatment of neurodegenerative disorders and CNS damage due to injury. Transplantation of new cells into the damaged CNS has the potential to repair damaged circuitries and provide neurotransmitters thereby restoring neurological function. It is also recognized in the art that transplantation into other tissue, such as eye tissue, offers the potential for treatment of degenerative disorders and tissue damage due to injury. Apps. 1 and 2 provide methods for generating more developmentally potent MSCs from less developmentally potent MSCs. The use of the cells of Apps. 1 or 2, or the cells of the instant invention specially stimulated for proliferation, migration or both in the treatment of neurological disorders and CNS damage, as well as the use of these MSCs in the treatment of other tissue damage or degeneration, can be demonstrated by the use of established animal models known in the art.

There are significant differences in the method of delivery to the brain and spinal cord of the cells prepared according to Apps. 1, 2 and the present invention, as well as the pyrimidine derivatives described herein, compared to the prior art. One exemplary difference is that the cells prepared according to Apps. 1, 2 and the present invention are transplanted intraventricularly. Further, while the transplantation of one or more separate more cells of Apps. 1, 2 or the instant invention is efficacious, such cells are preferably transplanted in the form of clusters of two or more cells via a surgical procedure, injection using a syringe large enough to leave the neurosphere-like clusters substantially intact, or insertion by catheter. The results disclosed in the examples below indicate that ventricular delivery of the cells of Apps. 1 or 2 or the cells of the present invention in cluster form can result in migration to the area of damage in the brain and proper neuronal differentiation. Further exemplified below is the effect of a pyrimidine derivative on the stimulation of proliferation and migration. Another benefit of intraventricular injection is less tissue destruction, resulting in less localized recruitment of immune cells by the host. This is evidenced by the lack of ventricular distortion, tumor formation, and increased host astrocyte staining without any immunosuppression.

The method of delivery of the cells of Apps. 1, 2 or the instant invention to the brain can be essentially duplicated for other immunoprivileged tissue such as, for example, the eye. Delivery of intact clusters of two or more cells via injection using a syringe large enough to leave the clusters substantially intact can result in migration to the area of damage in the eye and proper tissue-specific differentiation. Further, administration of pyrimidine derivatives according to the methods of the invention can substantially increase the proliferation of endogenous and exogenous MSCs.

There are examples in the art of intra-tissue injection (brain) of dissociated and partially differentiated NSCs (see, e.g., Benninger et al., 2000, *Brain Pathol.* 10: 330-341; Blakemore et al., 2000, *Cell Transplant.* 9: 289-294; Rosser et al., 2000, *Eur. J. Neurosci.* 12: 2405-2413; Rubio et al., 2000, *Mol. Cell. Neurosci.* 16: 1-13). In contrast, the methods of the instant invention employ injection of generally intact clusters because the dissociation of clusters, in the case of neural-lineage clusters of cells known as "neurospheres," can cause immediate senescence and increase the vulnerability of NSCs in culture. See, e.g., Svendsen et al., 1998, *J. Neurosci. Methods* 85: 141-152. As provided by this invention, intraventricular transplantation provides an alternative route to site-specific injection disclosed in the prior art. Using intraventricular transplantation, grafted cells can gain access to various structures by the flow of cerebrospinal fluid (CSF), and transplantation of NSCs prepared according to Apps. 1 and 2 or the present invention and administered according to the present invention in cluster form can act to prevent premature differentiation at inappropriate anatomical sites in the brain and central nervous system. Regarding the eye, intraocular administration of clusters of NSCs prepared according to Apps. 1 and 2 or the present invention, for example into the vitreous fluid, allows these multipotent cells to migrate to the area of degeneration or injury and differentiate appropriately.

Delivery of MSCs of Apps. 1 and 2 and of the present invention into other, non-immunoprivileged tissues can also be carried out, particularly when the MSCs are autologous to the recipient.

Functional integration of the graft into the host's neural tissue can be assessed by examining the effectiveness of grafts on restoring various functions, including but not limited to tests for endocrine, motor, cognitive and sensory functions. Useful motor tests include tests that quantitate rotational movement away from the degenerated side of the brain, and tests that quantitate slowness of movement, balance, coordination, akinesia or lack of movement, rigidity and tremors. Cognitive tests include tests of the ability to perform everyday tasks, as well as various memory tests, including maze performance such as the Morris water maze performance. For example, using the cells and methods of Apps. 1 and 2, MNSCs injected into the ventricle of 24-month-old rats after in vitro expansion displayed extensive and positional incorporation into the aged host brain with improvement of cognitive score (FIG. 1), as assessed by the Morris water maze after 4 weeks of the transplantation. Results of the experiments disclosed herein indicate that the aged brain is capable of providing the necessary environment for MSCs of Apps. 1 and 2 and the present invention to retain their multipotent status and demonstrate the potential for neuroreplacement therapies in age associated neurodegenerative disease.

Functional integration of the graft into the host's other tissue can be assessed by examining the effectiveness of grafts on restoring various functions specific to the injured or degenerated tissue, for example improvement in sight for transplantation of stem cells of the invention to the eye. Using the methods of the present invention, substantial stimulation of proliferation of endogenous stem cells can be observed in the eye with administration of a pyrimidine derivative as disclosed herein.

As assessed by the Morris water maze test, improvement in spatial memory of MSC-transplanted animals (which cells were prepared according to Apps. 1 or 2, and apply to the cells of the instant invention) was accompanied by incorporation of the MSCs into the brain areas known to be related to spatial memory. The post-transplant morphology of rat brain tissue indicates that functional association of the transplanted cells to the host brain occurs. Immunohistochemical analysis revealed that the bIII-tubulin-positive donor-derived cells found in the cerebral cortex are characterized by having dendrites pointing to the edge of the cortex whereas in the hippocampus, donor-derived neurons exhibited morphologies with multiple processes and branches. These differential morphologies of the transplanted MSCs in different brain regions indicate that site-specific differentiation of the MSCs occurs according to various factors present in each brain region.

Strong astrocyte staining was also found in the frontal cortex layer 3 and CA2 region of hippocampus in rat brains transplanted with MSCs of Apps. 1 and 2, areas where astrocytes are not normally present in the animal. Migration of the more developmentally potent cells to the CA2 is of particular interest because CA2 pyramidal neurons highly express bFGF, and the expression of bFGF is up-regulated by entorhinal cortex lesions (see, e.g., Eckenstein et al., 1994, *Biochem. Pharmacol.* 47: 103-110; Gonzalez et al., 1995, *Brain Res.* 701: 201-226; Williams et al., 1996, *J. Comp. Neurol.* 370: 147-158). CA2 pyramidal neurons in the host brain can express bFGF as a response to a reduction of synaptic transmission, an event that can occur during aging. Subsequently, this expressed bFGF can act as a signal for transplanted MSCs of Apps. 1 and 2 or the present invention to respond, migrate or proliferate under the influence of bFGF produced in the host brain after the transplantation.

Figure 2:
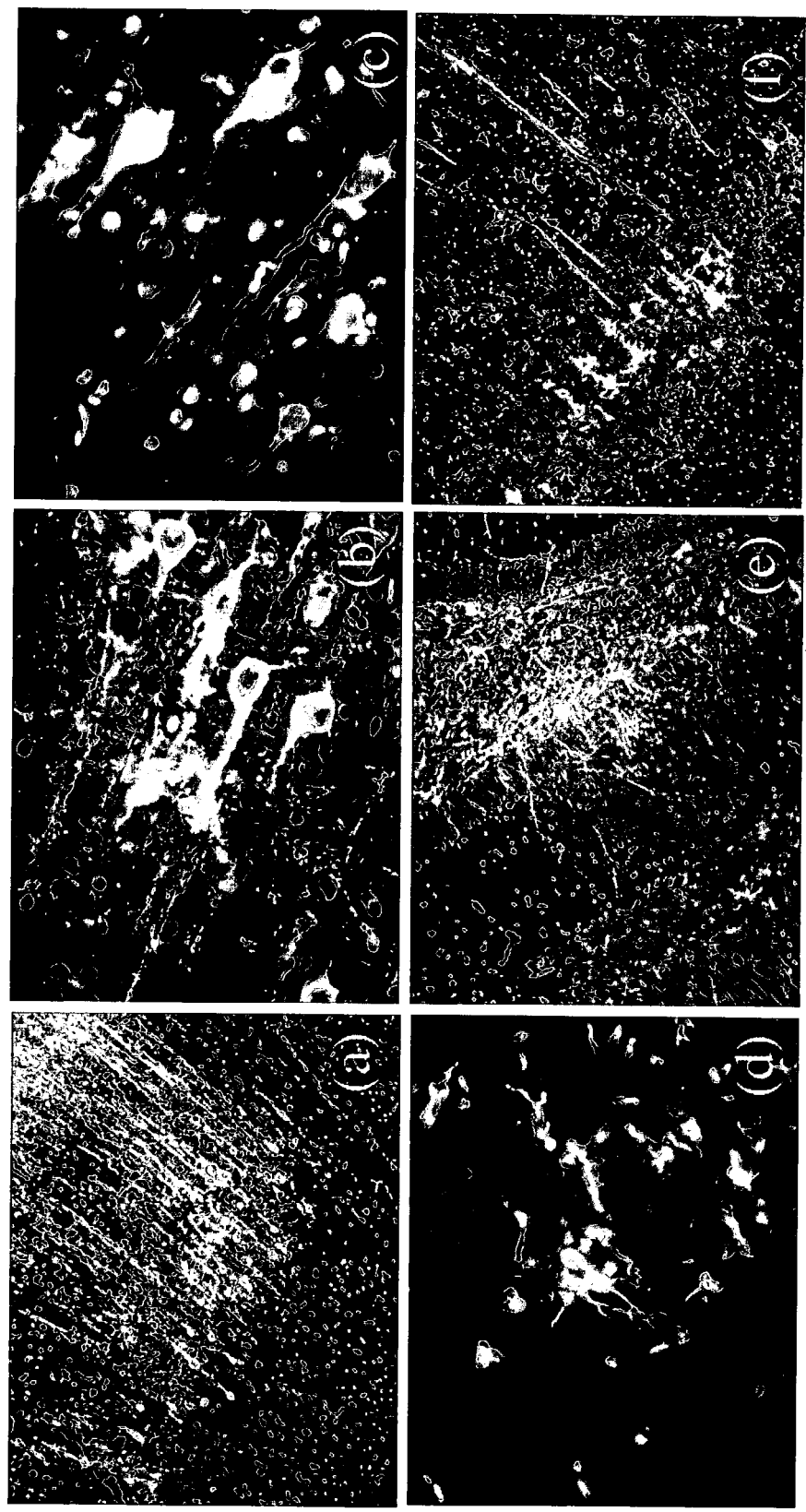
FIG. 2 shows typical fluorescent immunohistochemical photomicrographs of aged rat brain 30 days after transplantation of MNSCs of the co-owned and co-pending U.S. patent application referenced above. bIII-tubulin and GFAP immunoreactivity were used as markers for neuron and glia, respectively. (a) MNSCs of the co-owned and co-pending U.S. patent application migrated into the cortex and differentiated into neurons as indicated by the bIII-tubulin positive cells (green), which have morphologies typical of pyramidal cells in layer IV and V of the parietal cortex. Apical dendrites were pointed towards to the edge of the cortex. Since the NSCs were pre-treated with BrdU, the transplanted cells have BrdU positive nuclei (red). Contrarily, the host cell's nuclei are counter stained with DAPI (blue). Many cells having BrdU positive nuclei are observed with bIII-tubulin immunoreactivity in layer II and without bIII-tubulin immunoreactivity in layer III. (b, c) Higher magnification of the parietal cortex in cortex layer IV: all the bIII-tubulin immunoreactive (green) positive cells show BrdU (red) positive nuclei while many other host cell's nuclei are stained with only DAPI (blue). (d) MNSCs according to said co-owned and co-pending U.S. patent application migrated into the hippocampus and differentiated into bIII-tubulin positive cells (green), in CA1 pyramidal cell layer. These bIII-tubulin positive cells have BrdU positive nuclei (red), indicating that these cells originated from transplanted cells. In contrast, host cell nuclei counter stained with DAPI (blue) are not bIII-tubulin positive. (e) In the dentate gyrus many fibers were bIII-tubulin positive in addition to the bIII-tubulin positive cells (green) and GFAP positive sells (red). (f) bIII-tubulin positive cells (green) and GFAP positive cells (red) were found in layer IV and layer III, respectively. Such a layer of astrocytes was not observed in normal rats without NSC transplantation. Again, the methods of the instant invention can act to increase the number of such exogenously transplanted, BrdU-treated cells in vivo, as well as enhance their number while being treated according to the methods of the co-owned and co-pending application. The methods of the instant invention can also increase the abundance of the endogenous NSC population.

The regions rich in astrocyte staining in transplanted rat brains are the same regions where extensively stained neuronal fibers were identified (FIGS. 2a, 2d and 2e). During development, glial cells have many complex functions, such as neuronal and axonal guidance and production of trophic factors (see, e.g., Pundt et al., 1995, *Brain Res.* 695: 25-36). This overlapping distribution of glial and neuronal fibers strongly suggests that this interaction plays a pivotal role in survival, migration, and differentiation of the transplanted MSCs.

Immunohistochemistry of transplanted rat brains reveals a symmetrical distribution of neurons and astrocytes at both sides of the host brain, indicating that the progeny of the more developmentally potent cells of Apps. 1, 2 (and those of the present invention) can migrate. Although astrocytes have been shown to migrate over long distances following transplantation (see, e.g., Blakemore et al., 1991, *Trends Neurosci.* 14: 323-327; Hatton et al., 1992, *Glia* 5: 251-258; Lundberg et al., 1996, *Exp. Neurol.* 139: 39-53), there is experimental evidence showing that neurons do not migrate as widely as glial cells (see, e.g., Fricker et al., 1999, *J. Neurosci.* 19: 5990-6005). As disclosed herein, cells derived from the MSCs of Apps. 1 and 2 possess similar migratory capacity to astrocyte precursors.

As MSCs of Apps. 1 and 2 and the present invention can mimic neural stem cells in many regards, relevant information pertaining to neural stem cells is presented, followed by information pertaining to mesenchymal and retinal stem cells. One of skill in the art will readily recognize the methods of the invention are not limited to these three types of stem cells and instead extend to cover all cell types not yet terminally differentiated.

Neural-Related

Due to the generally low proliferation rate of mammalian NSCs, there is a correlation between advancing age and impaired brain function even in the absence of specific neurodegenerative disease or physical or biological brain trauma. Apps. 1 and 2 and the present invention provide methods for counteracting impaired brain function due to advancing age through the addition of MSCs (of Apps. 1 and 2 and the present invention) capable of proliferation, migration and differentiation in mammalian brain when introduced thereto.

Physical trauma and biological trauma are additional causes of impaired or improper brain function. The term "physical trauma" denotes brain cell damage due to external sources such as blunt head trauma, severe concussion and the like. Such physical trauma can be localized or general depending on the source and severity of the trauma. The term "biological trauma" denotes any acute brain injury that has its origin in a biological process, for example, stroke, aneurysm, epilepsy, brain tumor, hypoxia and the like.

Another source of impaired or improper brain function is neurodegenerative disease. In recent years neurodegenerative disease has become an important concern due to an expanding elderly population that is at greatest risk for these disorders. Neurodegenerative diseases include, but are not limited Alzheimer's disease, amyotrophic lateral sclerosis (ALS), Parkinson's disease, Pick's disease, Huntington's disease, progressive supranuclear palsy, corticobasal degeneration, Parkinson-ALS-dementia complex, Gerstmann-Straussler-Scheinker syndrome, Hallervorden-Spatz disease, Kufs' disease, Wilson's disease, multiple sclerosis (MS), late-onset metachromatic leukodystrophy and adrenoleukodystrophy. The effects of these diseases can be counteracted by administration of the MSCs of Apps. 1 and 2 and the present invention.

There are a variety of organic brain diseases that impair motor or cognitive function. Degeneration in the basal ganglia can lead to diseases with cognitive and motor symptoms, depending on the exact location of the degeneration. Motor deficits are a common result of degeneration in the basal ganglia. Huntington's chorea is associated with the degeneration of neurons in the striatum, which leads to involuntary jerking movements in the host. Degeneration of a small region called the subthalamic nucleus is associated with violent flinging movements of the extremities in a condition called ballismus, while degeneration in the putamen and globus pallidus is associated with a condition of slow writhing movements or athetosis. In Parkinson's disease, degeneration is seen in another area of the basal ganglia, the substantia nigra par compacta. This area normally sends dopaminergic connections to the dorsal striatum, which are important in regulating movement. Therapy for Parkinson's disease has centered upon restoring dopaminergic activity to this circuit, which can be accomplished by transplantation of neural stem cells to this region of the brain according to the instant invention In Alzheimer's disease, another neurodegenerative disease, there is substantial cellular degeneration of the forebrain and cerebral cortex. Further, a localized area of the basal ganglia, the nucleus basalis of Meynert, appears to be selectively degenerated. This nucleus normally sends cholinergic projections to the cerebral cortex, which are thought to participate in cognitive functions including memory.

Mesenchymal Related

Although adult stem cells continue to possess some multipotency, cell types produced from adult stem cells are limited by their tissue-specific character. For example, human NSCs spontaneously differentiate into brain cells under basal media conditions, but MeSCs cannot spontaneously differentiate into neural cells without the addition of certain factors. These results indicate that each stem cell contains specific information that would allow it to become a special type of cell, i.e., they are partially committed to become a particular type of cell in a tissue-specific manner. To overcome this barrier of stem cell lineage, alterations to the cells and their environment are necessary. However, the exact regulation mechanisms of tissue-specific stem cell fate decisions remain unclear. The absence of this knowledge creates an important problem, because although MeSCs are rather easy to isolate from bone marrow and to proliferate in culture, they cannot naturally differentiate into NSCs or other non-mesenchymal-lineage cells. Although the potential therapeutic use of MeSCs in the central nervous system has been discussed, technologies to induce neural lineage in MeSCs had not been fully established prior to Apps. 1 and 2. The present invention provides methods stimulating proliferation, migration or both proliferation and migration of the endogenous stem cell population or populations of exogenously introduced cells, such as, for example, the cells of Apps. 1 or 2.

MeSCs prepared according to the methods of App. 1 can serve as an alternative to NSCs for potential therapeutic use utilizing the methods of App. 1 and the present invention, which exploit the capacity of substituted deoxyuridine species, such as BrdU, to prime the MeSCs, i.e., remove them from their restricted mesenchymal differentiation path to the neural stem cell-like (or other lineage, i.e., make them more developmentally potent) differentiation path and pyrimidine derivatives, which stimulate them to proliferate and migrate far above wild-type rates. MeSCs were successfully differentiated into neurons and glia in vitro and in vivo using the substituted deoxyuridine pretreatment of App. 1. Thus, MeSCs of App. 1 can serve as an alternative to NSCs for potential therapeutic use in neuroreplacement utilizing the methods of App. 1 and the present invention.

The methods of the instant invention are important in the neuroreplacement field because they enable the expansion of endogenous stem cell numbers in vivo. Further, the methods of the invention are important in the neuroreplacement field because they enable the stimulation of proliferation and migration in exogenously introduced, developmentally potent, stem cell populations such as those of Apps. 1 or 2. Since the pyrimidine derivative, as used in the instant invention, can be used on various stem cell populations, the invention is not only useful to neuroreplacement but to other kinds of tissue regeneration or replacement as well.

Retinal Related

Retinal degenerative diseases, including macular degeneration, are major causes of blindness. Despite investigations into gene therapy, growth/survival factor injections and vitamin treatments, no effective vision-restoring treatments are currently available. Visual impairment caused by the degeneration of photoreceptors or neural cells has been considered incurable because of a long-held "truism" that neurons do not regenerate during adulthood. However, this statement has been challenged and there is new evidence that these cells do indeed have the potential to be renewed after maturation, thus opening a door for the development of novel therapies to treat visual impairment by retinal regeneration using stem cell transplantation.

The capacity for retinal regeneration in cold-blooded vertebrates has long been recognized. Fish and amphibians continue to make new retinal neurons through a population of retinal stem cells residing at the peripheral margin of the retina, the so-called "ciliary marginal zone." Recent studies have provided evidence that birds and adult mammals also possess a zone of cells at the retinal margin analogous to the ciliary marginal zone of cold-blooded vertebrates. These retinal stem cells are reported not only to generate photoreceptor and other retinal cells in vitro, but also to differentiate into retinal cells following transplantation into the retinal area. Although these results indicate the possibility of retinal regeneration therapy, an alternative source of stem cells, or a means to increase the number of endogenous retinal stem cells, is required for clinical applications because the number of retinal stem cells is limited.

Neural stem cells have been isolated from embryonic and adult mammalian brains and have been propagated in vitro in a variety of culture systems. Using a serum-free unsupplemented media condition, NSCs spontaneously differentiated into bIII-tubulin-, glial fibrillary acidic protein (GFAP)-, and O4-immunopositive cells, markers for neurons, astrocytes, and oligodendrocytes, respectively. MSCs treated according to methods of Apps. 1 and 2 migrate and differentiate into neurons and glia after transplantation into the brains of 24-month-old rats and significantly improved the cognitive functions of these animals. This result suggested that MSCs produced according to Apps. 1 and 2 could provide transplantable material to produce a retinal stem cell alternative.

There are variety of factors involved in the development of retinal tissue that regulate the proliferation and differentiation of retinal cells. Transforming growth factor beta 3 (TGF-b3) is thought to regulate cell proliferation during development and also influence the commitment or the differentiation, or both, of neural progenitor cells to retinal fates. Treatment of embryonic day-18 rat retinal cultures with TGF beta-like protein, activin A, causes the progenitor cells in these cultures to exit the cell cycle and differentiate into rod photoreceptors, indicating that the TGF family is an important regulator of photoreceptor differentiation in the developing retina. Treatment of the NSCs prepared according to Apps. 1 and 2 can be induced to adopt a retinal differentiation path through exposure to the above factors. Utilizing the methods and reagents of the present invention, both exogenous MSCs, like those prepared according to Apps. 1 and 2, and endogenous stem cells of the eye can be stimulated to proliferate and migrate beyond wild-type levels.

Previous transplantation studies of NSCs into retinal tissue with rd mice (a model of retinitis pigmentosa), mechanical lesions, transient ischemia and normal retina have revealed that donor cells migrate into the retinal area and differentiate into neurons and glia, but they did not show any retinal cell markers. These results indicated that NSCs are already committed to become neural tissue, and that this commitment is not mutable solely by transplantation into the retina. Thus, to differentiate NSCs (or cells of alternate origin, such as MeSCs) into retinal cells, alteration of their epigenetic information before retinal transplantation appeared necessary, something accomplished by the methods of Apps. 1 and 2. Using the methods of Apps. 1 and 2, NSCs or easily obtainable MeSCs, i.e., can be transformed into MSCs and subsequently used as alternatives to retinal stem cells to repair ocular tissue damage or promote tissue regeneration. Treatment of endogenous multipotent stem cells populations in vivo or the multipotent stem cells of Apps. 1 or 2 in vitro according to the methods of the present invention, can enhance their number and/or migration and hence increase their efficacy in repairing damaged tissue in the eye.

The inventive methods of Apps. 1 and 2 use BrdU and other substituted deoxyuridines to change the cell fate decisions of stem cells. In the case of retinal transplants, these MSCs are treated with TGF-b3 to encourage their commitment change into the various cell types found in eye tissue, inter alia, chorid, Buchs and retinal pigment epithelium cells, rod and cone photoreceptor cells, horizontal cells, bipolar neurons, amacrine, ganglion and optic nerve cells. These non-limiting, exemplary cell types found in eye tissue are collectively referred to as retinal cells. These results are enhanced by the methods of the present invention wherein the number of MSCs competent to migrate and differentiate appropriately is increased due to stimulated proliferation.

There are a variety of neurological and corporal deficits that can be addressed using the MSCs of Apps. 1 and 2 and the present invention.

"Neurological Deficits" Amenable to Treatment

Because the invention relates in part to the discovery that multipotent precursor cells can be stimulated to proliferate and migrate through the brain and other tissues, such MSCs can be used to treat neurological deficits caused by a wide variety of diseases, disorders, and injuries. These insults include, but are not limited to, the following.

Degenerative Diseases

Degenerative diseases that can be treated according to the methods of the invention include Alzheimer's disease (AD), Parkinson's disease (PD), Huntington's disease (HD), Pick's disease, progressive supranuclear palsy (PSP), striatonigral degeneration, cortico-basal degeneration, childhood disintegrative disorder, olivopontocerebellar atrophy (OPCA; including a heritable form), Leigh's disease, infantile necrotizing encephalomyelopathy, Hunter's disease, mucopolysaccharidosis, various leukodystrophies (such as Krabbe's disease, Pelizaeus-Merzbacher disease, and the like), amaurotic (familial) idiocy, Kuf's disease, Spielmayer-Vogt disease, Tay Sachs disease, Batten disease, Jansky-Bielschowsky disease, Reye's disease, cerebral ataxia, chronic alcoholism, beriberi, Hallervorden-Spatz syndrome, and cerebellar degeneration.

Traumatic and Neurotoxic Injuries to the Central Nervous System

Traumatic and neurotoxic injuries that can be treated according to the methods of the invention include gunshot wounds, injuries caused by blunt force, injuries caused by penetration injuries (e.g., stab wounds), injuries caused in the course of a surgical procedure (e.g., to remove a tumor or abscess from the CNS or to treat epilepsy), poisoning (e.g., with MPTP or carbon monoxide), shaken-baby syndrome, adverse reactions to medication (including idiosyncratic reactions), drug overdose (e.g., from amphetamines), and post-traumatic encephalopathy.

Ischemia

Any disruption of blood flow or oxygen delivery to the nervous system can injure or kill cells, including neurons and glial cells, therein. These injuries can be treated according to the methods of the present invention and include injuries caused by a stroke (including a global stroke (as may result from cardiac arrest, arrhythmia, or myocardial infarction) or a focal stroke (as may result from a thrombus, embolus, hemorrhage, or other arterial blockage)), anoxia, hypoxia, partial drowning, myoclonus, severe smoke inhalation, dystonias (including heritable dystonias), and acquired hydrocephalus.

Developmental Disorders

Developmental disorders that can be treated according to the methods of the invention include schizophrenia, certain forms of severe mental retardation, cerebral palsy (whether caused by infection, anoxia, premature birth, blood type incompatibility: etc. and whether manifest as blindness, deafness, retardation, motor skill deficit, etc.), congenital hydrocephalus, metabolic disorders affecting the CNS, severe autism, Down Syndrome, LHRH/hypothalamic disorder, and spina bifida.

Disorders Affecting Vision

Disorders affecting vision, particularly those caused by the loss or failure of retinal cells, can be treated according to the methods and cells of the invention. These disorders include, for example, diabetic retinopathy, serious retinal detachment, retinal damage associated with glaucoma, traumatic injury to the retina, retinal vascular occlusion, macular degeneration (wet or dry), post-surgical healing, tumor, heritable retinal dystrophies, optic nerve atrophy, and other retinal degenerative diseases. Cells targeted for repair utilizing cells and methods of the invention include, for example, choroids, Buchs, retinal pigment epithelial (RPE), rods, cones, horizontal cells, bipolar neurons, amacrine, ganglion, and optic nerve.

Injuries and Diseases of the Spinal Cord

Injuries to or diseases affecting the spinal cord can also be treated according to the methods of the invention. Such injuries or diseases include post-polio syndrome, amyotrophic lateral sclerosis, nonspecified spinal degeneration, traumatic injury (such as those caused by automobile or sporting accidents), including any injury that crushes, partially severs, completely severs, or otherwise adversely affects the function of cells in the spinal cord), injuries caused by surgery to the spinal cord (e.g., to remove a tumor), anterior horn cell disease, and paralytic diseases.

Demyelinating or Autoimmune Disorders

Neurological deficits caused by demyelination or an autoimmune response can be treated according to the methods of the invention. Such deficits can be caused by multiple sclerosis, or lupus.

Infectious or Inflammatory Diseases

Neurological deficits caused by an infection or inflammatory disease can be treated according to the methods of the invention. Infections or inflammatory diseases that can cause treatable deficits include Creutzfeldt-Jacob disease and other slow virus infectious diseases, AIDS encephalopathy, post-encephalitic Parkinsonism, viral encephalitis, bacterial meningitis and meningitis caused by other organisms, phlebitis and thrombophlebitis of intracranial venous sinuses syphilitic Parkinsonism, and tuberculosis of the CNS.

In addition to the deficits, diseases and disorders set forth explicitly above, those of ordinary skill in the art are well able to recognize neurological deficits, regardless of their cause, and to apply the methods of the present invention to treat patients who have such deficits. In addition to the conditions listed above, that are amenable to treatment with the methods described herein, neurological deficits can be caused by Lesch-Nyhan syndrome, myasthenia gravis, various dementias, numerous parasitic diseases, and epilepsy. Further, alleviation of age-related memory loss is an object of the invention. The methods of the invention can be readily applied to alleviate neurological deficits caused by these and other diseases, disorders, or injuries.

"Corporal Deficits" Amenable to Treatment

The invention also relates to the amelioration of corporal deficits utilizing multipotent precursor cells stimulated to divide, migrate through damaged tissue and differentiate in a tissue-specific manner. Cells according to the invention can be used to treat corporal deficits caused by a wide variety of diseases, disorders, and injuries, the result of which is trauma, malfunction, degeneration or loss of muscle such as, for example, cardiac muscle due to myocardial infarction. Other examples include malfunction, degeneration or loss of other cells and tissues apart from those discussed in the neurological deficit section above such as, for example, internal organs. For example, liver function can be adversely affected by, among other things, disease (e.g., cirrhosis or hepatitis), trauma or age. Other exemplary internal organs amenable to treatment utilizing the embodiments of the invention include heart, pancreas, kidney, stomach, and lung. Corporal deficits also comprise malfunction, degeneration or loss of skeletal assets such as, for example, vertebrae.

An advantage of the cells of the invention is that they can be genetically engineered according to routine procedures known in the art (See, e.g., Sambrook et al., 2001, MOLECULAR CLONING: A LABORATORY MANUAL. 3rd ed., Cold Spring Harbor Laboratory Press: N.Y.). In certain embodiments, constructs encoding proteins of interest can be provided to the cells. In other embodiments, constructs that inhibit expression of undesired proteins can be provided (such as, for example, ribozymes and antisense molecules). In further embodiments, drug resistance genes and markers, or detectable markers such as GFP can be provided. Preferably, the marker and other genes are operably and genetically linked to gene expression regulatory elements (including but not limited to promoters and enhancers) that are operable in a terminally differentiated cell derived from the MNSCs of the invention or in the undifferentiated MNSCs of the invention or both.

The following examples are presented in order to more fully illustrate the preferred embodiments of the invention. They should in no way be construed, however, as limiting the scope of the invention, as defined by the appended claims.

EXAMPLES

Example 1

Improvement of Cognitive Function in Aged Rat by the Transplantation of NSCs of the Invention Human NSCs do not require any exogenous factors for differentiation and survived more than three weeks in basal media without the addition of any factor to support their survival (Qu et al., 2001, *Neuroreport* 12: 1127-32). Thus, it appears that human NSCs produce factors to differentiate and support themselves, which suggested that these cells could be transplanted into aged animals after treatment according to the methods of Apps. 1, 2 and the present invention.

Human NSCs, expanded without differentiation under the influence of mitogenic factors in supplemented serum-free media and pretreated by the incorporation of bromodeoxyuridine (BrdU) into the nuclear DNA, were injected into the lateral ventricle of mature (6-month-old) and aged (24-month-old) rats. Human NSCs prepared according to the methods of the invention survived 30 days after xenotransplantation into aged rat brain, while retaining both multipotency and migratory capacity, and also improved cognitive function in 24-month-old rats. Cognitive function of the animals was assessed by the Morris water maze both before and four weeks after the transplantation of human NSCs of the invention. Before human NSC transplantation, some aged animals (aged memory unimpaired animals) cognitively functioned in the range of mature animals, while others (aged memory impaired animals) functioned entirely out of the cognitive range of the mature animals. After transplantation of the BrdU-treated human NSCs, most aged animals had cognitive function in the range of the mature animals. Strikingly, one of the aged memory-impaired animals showed dramatic improvement in its behavior, functioning even better than the mature animals (FIG. 1a). Statistical analysis showed that cognitive function was significantly improved in both mature and aged memory impaired animals but not in aged memory-unimpaired animals after BrdU-treated human NSC transplantation (FIG. 1b), which may be due to the physical limitations of the aged animals. The performance of three of the aged animals deteriorated in the water maze after transplantation of treated human NSCs. It is possible that the physical strength of these animals deteriorated during the experimental period.

These behavioral results indicate the beneficial effects of the transplantation of BrdU-treated human NSCs into the host brain. After the second water maze task, postmortem brains were further analyzed by immunohistochemistry for human bIII-tubulin and human GFAP, markers for neurons and astrocytes respectively. There was no sign of ventricular distortion, no evidence of tumor formation, and no strong host anti-graft immunoreactivity was observed as revealed by weak host astrocyte staining. Intensely and extensively stained with bIII-tubulin, neurons with BrdU-positive nuclei were found in bilateral singular and parietal cortexes (FIG. 2a-c) and hippocampus (FIG. 2d,e). The bIII-tubulin-positive neurons found in the cerebral cortex were typified by a dendrite pointing to the edge of the cortex. In the hippocampus, donor-derived neurons exhibited multiple morphologies, varying in cellular size and shape, and one or more processes and branching.

Generally, GFAP-positive astrocytes were localized near the area where neuronal cells were found. On further analysis (overlapping images of their distributions), donor-derived astrocytes were found to co-localize with neuronal fibers in the cortex (FIG. 2f). These astrocytes were larger than the host glia, with cell bodies 8-10 microns in diameter and thick processes. Some of these astrocytes had a unilateral morphology (asymmetric), and the immunostaining formed a thin ring around the nucleus, while the majority of the processes were formed on the other side. Most cells appeared a symmetrical with processes forming from all sides. The absence of this type of cell in normal animal without the transplantation of treated human NSCs was confirmed using immunohistochemistry for rat astrocytes. Host astrocytes had small cell bodies with multiple delicate processes, and were distributed throughout the brain mainly in white matter and around the edges of the brain.

These results demonstrated that transplanted cells of Apps. 1 and 2 migrated in rat brain and differentiated into appropriate cell types. The concomitant improvement in cognitive function indicated that transplanted MSCs of Apps. 1 and 2 were functionally integrated into the recipient brains.

The Morris Water Maze:

The Morris water maze consists of a large circular tank (diameter, 183 cm, wall height, 58 cm), filled with water (27° C.) and opacified by the addition of powdered milk (0.9 kg). Beneath the water surface (1 cm) near the center of one of the four quadrants of the maze a clear escape platform (height, 34.5 cm) is positioned. The rats receive three training trials per day for seven consecutive days, using a 60 sec inter-trial interval. A training trial consists of placing the animal in the water for 90 seconds or until the swimming rat successfully locates the platform. If the rat fails to find the platform within the 90 seconds, the animal is gently guided to the platform. For spatial learning assessment, the platform's location remains constant in one quadrant of the maze, but the starting position for each trial is varied. Every sixth trial is a probe trial, during which the platform is retracted to the bottom of the pool for 30 sec and then raised and made available for escape. The training trials assess the acquisition and day-to-day retention of the spatial task while the probe tests are used to assess search strategy. At the completion of a spatial learning assessment, one session with six trials of cue training is performed Rats are trained to escape to a visible black platform that is raised 2 cm above the surface of the water. The location of the platform is varied from trial to trial to assess sensorimotor and motivational functioning independent of spatial learning ability. Each rat is given 30 seconds to reach the platform and is allowed to remain there briefly before the 30 second inter-trial interval. Accuracy of performance is assessed using a learning index score computed from the probe trials. The learning index is a derived measure from average proximity (cumulative search error divided by the length of the probe trial) on the second, third, and fourth interpolated probe trials. Scores from these trials are weighted and summed to provide an overall measure of spatial learning ability. Lower scores on the index indicate a more accurate search near the target location; higher scores indicate a more random search and poor learning.

Cell Migration and Differentiation:

In order to investigate differentiation and/or migration of the cells of Apps. 1 or 2 in the brain, MSCs of those applications were transplanted into rodent brain. The animals were anesthetized with 50 mg/kg pentobarbital (i.p.) and mounted in a stereotaxic apparatus (David Kopf). Approximately $1\times10^4$ to $1\times10^5$ cells in 5 μl phosphate-buffered saline were injected into the ventricle using a microsyringe attached to the stereotaxic apparatus. After removing the hair from the surgical site using electric razor, an iodine swab was be applied to the area and a 0.5 cm surgical incision was made caudal to rostral in the skin at the surface of the cranium. The ventricle was stereotaxically localized using the following exemplary coordinates: AP=−0.58 mm from bregma, ML=+1 mm, and 2.4 mm below dura (for mouse): AP=−1.4 mm from bregma, ML=+3.3 mm, and 4.5 mm below dura (for rat). A 0.4-mm hole was made in the cranium by careful drilling. The cells of Apps. 1 or 2 were injected into the ventricle using a microsyringe. The injection was delivered over a period of five minutes and the needle was left in place for an additional two minutes following the injection. After the injection, the surgically incised skin was closed by Michel suture clip (2.5× 1.75 mm). Ten days post-surgery, proper healing of the incision site was observed, and the Michel sutures were removed.

The existence and location of the cells of Apps. 1 or 2 after administration in rat brain was analyzed as follows. At 30 days post-transplantation, the rats were sacrificed by an overdose of sodium pentobarbital (70 mg/kg, i.p.) and perfused with phosphate buffered saline (PBS) followed by 4% paraformaldehyde. Brains were removed and incubated overnight in 4% paraformaldehyde fixative containing 20% sucrose. The brains were sliced into 20 micron coronal sections using a cryomicrotome. The sections were washed briefly in PBS and pretreated with 1M HCl for 30 minutes at room temperature and neutralized with sodium borate (0.1 M, pH 8.0) for 30 minutes in order to increase the accessibility of an anti-BrdU antibody to BrdU incorporated in the cell nuclei. After rinsing with PBS, sections were transferred to absolution containing 0.25% Triton X-100 in PBS (PBST) for 30 minutes. The sections were then blocked by incubation in PBST containing 3% donkey normal serum for 1 hour, followed by incubating the sections overnight at 48° C. with sheep anti-BrdU (1:1000; Jackson IR Laboratories, Inc. West Grove, Pa.) or mouse anti-BrdU (1:200; DSHB, Iowa City, Iowa) diluted in PBST. After rinsing the sections in PBS, donkey anti-mouse or donkey anti-sheep conjugated to rhodamine IgG (Jackson IR Laboratories, Inc.) was added at a 1:200 dilution in PBST and the sections further incubated for 2 hours at room temperature in the dark.

The transplanted cells of Apps. 1 or 2, with BrdU immunopositive nuclei, were stained for human bIII-tubulin and human glial filament protein (GFAP). The sections were then washed with PBS and incubated with mouse IgG2b monoclonal anti-human bIII-tubulin, clone SDL3D10 (1:500, Sigma), goat antihuman GFAP, N-terminal human affinity purified (1:200, Research Diagnostics Inc., Flander, N.J.) or mouse IgG1 monoclonal anti-GFAP, clone G-A-5 (1:500, Sigma), respectively, overnight at 48° C. in the dark. After brief washing with PBS to remove excess primary antibody, the location of primary antibody binding was then determined using FITC-conjugated (Jackson IR Laboratories, Inc.) secondary antibody (donkey anti-mouse (1:200) or donkey anti-goat IgG (H+L; 1:200), respectively) by incubating the sections for 2 hours at room temperature in the dark.

The sections were then washed with PBS thoroughly before mounting to glass slides. The mounted sections were covered with Vectashield using 4',6-diamidine-2-phenylindole.2HCl (DAPI, Vector Laboratories, Inc., Burlingame, Calif.) for fluorescent microscopic observation. Microscopic images were taken by using an Axiocam digital camera mounted on the Axioscope 2 with Axiovision software (Zeiss).

NSC Culture:

NSCs were purchased (BioWhittaker, Walkersville, Md.), and alternatively isolated from human tissue, and cultured in a nonsupplemented, serum-free basal medium comprising HAMS-F12 (Gibco, BRL, Burlington, ON); antibiotic-antimycotic mixture (1:100, Gibco); B27 (1:50, Gibco); human recombinant FGF-2 and EGF (20 ng/ml each, R and D Systems, Minneapolis, Minn.) and heparin (5 ug/ml, Sigma, St. Louis, Mo.). The cells were incubated at about 37° C. in a 5% $CO_2$ humidified incubation chamber (Fisher, Pittsburgh, Pa.). To facilitate optimal growth conditions, NSC clusters were sectioned into quarters every 2 weeks and fed by replacing 50% of the medium every 4-5 days. To inhibit differentiation, the cells can be propagated on an uncoated flask or a flask that has been treated to repel the cells. To induce differentiation, these cells can be replated in the culture dishes (about $1\times10^5$ per dish) in the serum-free basal medium Eagle (BME), which comprises Earle's salt and L-glutamine, and cultured for about 5 days in the absence of FGF-2 and EGF and without the addition of other extrinsic differentiation factors. NSCs cultured in this serum-free medium can spontaneously undergo differentiation into neuronal cell types.

Example 2

Increase of Endogenous Stem Cell Proliferation by a Pyrimidine Derivative

Figure 3:
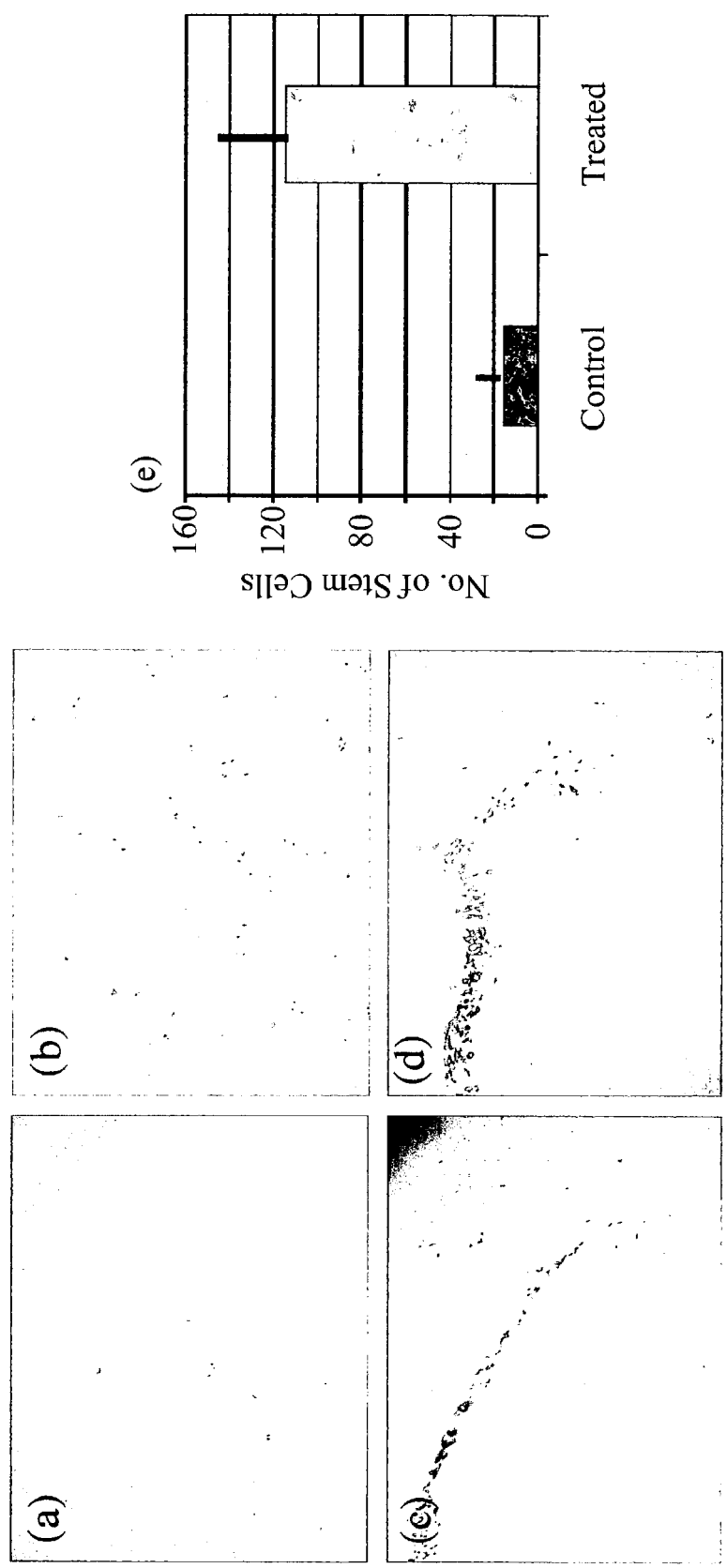
FIG. 3 shows the effects of MS-818 on endogenous neural stem cell populations in the brain. (a) Typical immunohistochemistry (×200) using BrdU (brown, marker for proliferating cells) in a control aged rat cerebral cortex without MS-818 treatment. (b) Typical immunohistochemistry (×200) using BrdU in an aged rat cerebral cortex with MS-818 treatment (3 mg/kg/day, i.p. for 5 days). The number of BrdU positive cells is significantly increased after MS-818 treatment. (c) Typical immunohistochemistry (×200) using BrdU (brown, marker for proliferating cells) in a control aged rat SVZ without MS-818 treatment. (d) Typical immunohistochemistry (×200) using BrdU in an aged rat SVZ with MS-818 treatment (3 mg/kg/day, i.p. for 5 days). The number of BrdU positive cells is increased after MS-818 treatment. (e) Quantitative analysis of the effects of MS-818 on a number of BrdU-positive cells in the cortex (a, b). There was a 7-fold increase in stem cell population after MS-818 treatment.
Figure 4:
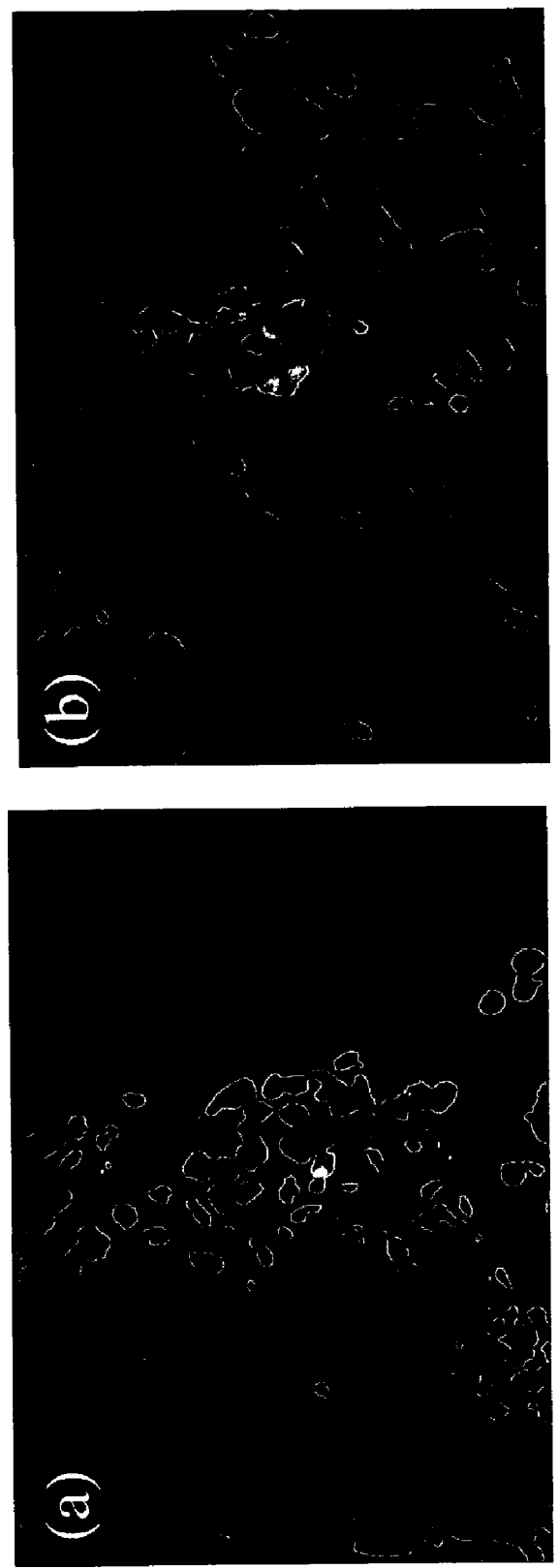
FIG. 4 shows the effects of MS-818 on endogenous retinal stem cell populations. (a) Typical immunohistochemistry (×400) using BrdU (red, marker for proliferating cells) in control rat retina without MS-818 treatment. (b) Typical immunohistochemistry (×400) using BrdU in rat retina with intraocular administration of MS-818 (10 µg/20 µl). The number of BrdU-positive cells is clearly increased after the treatment.

To investigate the effect of MS-818, a pyrimidine derivative, on stem cell population in vivo, MS-818 (3 mg/kg/day, i.p.) was injected for 5 days into aged (27-month old) male Fisher 344 rats. The same volume of saline was injected into control animals. Bromodeoxyuridine. (BrdU) (100 mg/kg/day i.p.) was then injected for 3 days. Twenty-four hours after the last injection, the brains were removed and fixed for immunohistochemical detection of the proliferating cells by immunostaining for BrdU. The number of BrdU positive cells increased more than seven fold in the cerebral cortices of MS-818-treated animals compared to those of controls (FIG. 3a,b,e), indicating an increased neural stem cell population in the brain. In the area of the subventricular zone, a significant increase not only in the proliferation but also in the migration of stem cells was found (FIG. 3c,d). When this compound was injected directly into the vitreous cavity (10 μg one time injection), a dramatic increase in the number of BrdU-positive cells was found in the retinal ciliary marginal zone (FIG. 4) after three days.

It should be understood that the foregoing disclosure emphasizes certain specific embodiments of the invention and that all modifications or alternatives equivalent thereto are within the spirit and scope of the invention as set forth in the appended claims.

What is claimed is:

1. A method of stimulating proliferation, migration or both proliferation and migration of exogenous neural stem cells or retinal stem cells or both neural and retinal stem cells in vivo, the method comprising administering an effective amount of a pyrimidine derivative of formula (1) or (2), or a pharmaceutically acceptable salt thereof, for an effective period to a mammal that has had more developmentally potent cells administered thereto

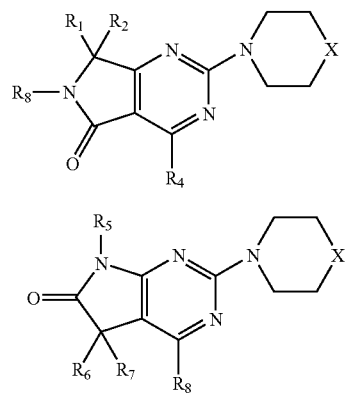

wherein R1 to R8 independently represent a hydrogen atom, a lower alkyl group, $CH_3OCH_2CH_2$—, $CH_2CONH_2$, —$COCH_3$, —$COC_2H_5$ or —$CH_2OCOC_2H_5$, and X represents NH, N—$CH_3$, N—$C_2H_5$, N-ph, N—$COOC_2H_5$, N—$SO_2CH_3$, $CH_2$, $CHCH_3$, $CHC_2H_5$, —O— or —S— in which ph stands for a phenyl group.

2. The method of claim 1, wherein the method stimulates proliferation of exogenous mammalian stem cells in vivo.

3. The method of claim 1, wherein the method stimulates migration of exogenous mammalian stem cells in vivo.

4. The method of claim 1, wherein the method stimulates proliferation and migration of exogenous mammalian stem cells in vivo.

5. A method of stimulating proliferation, migration or both proliferation and migration of mammalian neural stem cells or retinal stem cells or both neural and retinal stem cells in vitro, the method comprising contacting a mammalian stem cell with an effective amount of a pyrimidine derivative of formula (1) or (2), or a pharmaceutically acceptable salt thereof, for an effective period,

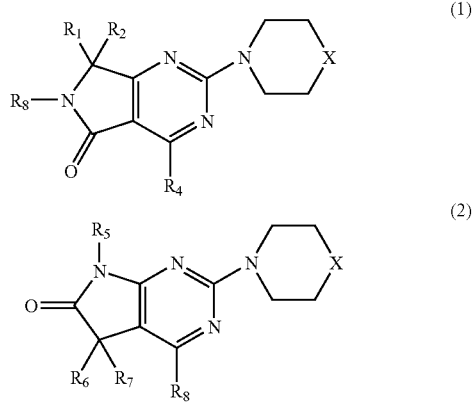

wherein R1 to R8 independently represent a hydrogen atom, a lower alkyl group, $CH_3OCH_2CH_2$—, $CH_2CONH_2$, —$COCH_3$, —$COC_2H_5$ or —$CH_2OCOC_2H_5$, and X represents NH, N—$CH_3$, N—$C_2H_5$, N-ph, N—$COOC_2H_5$, N—$SO_2CH_3$, $CH_2$, $CHCH_3$, $CHC_2H_5$, —O— or —S— in which ph stands for a phenyl group.

6. The method of claim 5, wherein the method stimulates proliferation of mammalian stem cells in vitro.

7. The method of claim 5, wherein the method stimulates migration of mammalian stem cells in vitro.

8. The method of claim 5, wherein the method stimulates proliferation and migration of mammalian stem cells in vitro.

9. The method of claim 5 further comprising the step of administering a growth factor.

10. The method of claim 9 wherein the growth factor is fibroblast growth factor, epidermal growth factor or a combination thereof.

11. The method of claim 9 where in the growth factor is a combination of fibroblast growth factor and epidermal growth factor.

12. The method of claim 9 wherein the growth factor is fibroblast growth factor.

13. The method of claim 9 wherein the growth factor is epidermal growth factor.

14. The method of claim 5 further comprising the step of contacting the mammalian stem cell with heparin.

* * * * *